US011448643B2

(12) United States Patent
Bhatia et al.

(10) Patent No.: US 11,448,643 B2
(45) Date of Patent: Sep. 20, 2022

(54) METHODS TO SPECIFICALLY PROFILE PROTEASE ACTIVITY AT LYMPH NODES

(71) Applicant: Massachusetts Institute of Technology, Cambridge, MA (US)

(72) Inventors: Sangeeta N. Bhatia, Lexington, MA (US); Darrell J. Irvine, Arlington, MA (US); Karl Dane Wittrup, Chestnut Hill, MA (US); Andrew David Warren, Cambridge, MA (US); Jaideep S. Dudani, Boston, MA (US); Naveen K. Mehta, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 16/091,145

(22) PCT Filed: Apr. 7, 2017

(86) PCT No.: PCT/US2017/026564
§ 371 (c)(1),
(2) Date: Oct. 4, 2018

(87) PCT Pub. No.: WO2017/177115
PCT Pub. Date: Oct. 12, 2017

(65) Prior Publication Data
US 2019/0128873 A1 May 2, 2019

Related U.S. Application Data

(60) Provisional application No. 62/319,820, filed on Apr. 8, 2016.

(51) Int. Cl.
| | | |
|---|---|---|
| *C12Q 1/37* | (2006.01) | |
| *G01N 33/50* | (2006.01) | |
| *C07K 14/00* | (2006.01) | |
| *G01N 33/574* | (2006.01) | |
| *C07K 7/00* | (2006.01) | |
| *C07K 7/06* | (2006.01) | |
| *C07K 7/08* | (2006.01) | |
| *B82Y 5/00* | (2011.01) | |

(52) U.S. Cl.
CPC .......... *G01N 33/5088* (2013.01); *C07K 7/00* (2013.01); *C07K 7/06* (2013.01); *C07K 7/08* (2013.01); *C07K 14/001* (2013.01); *C12Q 1/37* (2013.01); *G01N 33/574* (2013.01); *B82Y 5/00* (2013.01); *C07K 2319/31* (2013.01); *C07K 2319/50* (2013.01); *G01N 2333/96425* (2013.01)

(58) Field of Classification Search
None
See application file for complete search history.

(56) References Cited

U.S. PATENT DOCUMENTS

| | | | |
|---|---|---|---|
| 5,500,161 A | 3/1996 | Andrianov et al. | |
| 5,811,252 A | 9/1998 | Verheijen | |
| 5,885,775 A | 3/1999 | Haff et al. | |
| 6,312,390 B1 | 11/2001 | Phillips | |
| 6,335,429 B1* | 1/2002 | Cai ........................ | C12Q 1/68 435/18 |
| 6,592,847 B1 | 7/2003 | Weissleder et al. | |
| 6,597,996 B1 | 7/2003 | Venkataraman et al. | |
| 6,629,040 B1 | 9/2003 | Goodlett et al. | |
| 6,824,981 B2 | 11/2004 | Chait et al. | |
| 7,041,453 B2 | 5/2006 | Yang | |
| 7,169,892 B2* | 1/2007 | Atsushi ................ | A61K 9/1271 435/176 |
| 7,179,655 B2 | 2/2007 | Patricelli | |
| 7,329,506 B2 | 2/2008 | William | |
| 7,412,332 B1 | 8/2008 | Venkataraman et al. | |
| 7,456,269 B2 | 11/2008 | Gurney et al. | |
| 7,468,258 B2 | 12/2008 | Owen | |
| 7,544,518 B2 | 6/2009 | Aebersold et al. | |
| 7,595,155 B2 | 9/2009 | Murakami | |
| 7,879,574 B2 | 2/2011 | Packard et al. | |
| 7,985,401 B2 | 7/2011 | Jiang et al. | |
| 8,673,267 B2 | 3/2014 | Bhatia et al. | |
| 8,841,085 B2 | 9/2014 | Kwon et al. | |
| 8,969,027 B2 | 3/2015 | Bossmann et al. | |
| 9,006,415 B2 | 4/2015 | Ren et al. | |
| 9,072,792 B2 | 7/2015 | Jiang et al. | |
| 9,155,471 B2 | 10/2015 | Lee et al. | |
| 9,657,326 B2 | 5/2017 | Ruether et al. | |
| 9,808,532 B2 | 11/2017 | Tsien et al. | |
| 9,913,917 B2 | 3/2018 | Groves et al. | |
| 9,970,941 B2 | 5/2018 | Bhatia et al. | |
| 10,006,916 B2 | 6/2018 | Kwong et al. | |
| 10,527,619 B2 | 1/2020 | Bhatia et al. | |
| 10,883,998 B2 | 1/2021 | Bhatia et al. | |
| 11,054,428 B2 | 7/2021 | Bhatia et al. | |

(Continued)

FOREIGN PATENT DOCUMENTS

| | | |
|---|---|---|
| CN | 102558362 A | 7/2012 |
| CN | 103012595 A | 4/2013 |

(Continued)

OTHER PUBLICATIONS

Warren et al. 2014 (Point-of-care diagnostics for noncommunicable diseases using synthetic urinary biomarkers and paper microfluidics; PNAS 111 (10) 3671-3676). (Year: 2014).*

(Continued)

*Primary Examiner* — Mary Maille Lyons
(74) *Attorney, Agent, or Firm* — Wolf, Greenfield & Sacks, P.C.

(57) ABSTRACT

In some aspects, the disclosure provides compositions and methods for detecting and monitoring the activity of pro teases in vivo using affinity assays. The disclosure relates, in part, to the discovery that biomarker nanoparticles targeted to the lymph nodes of a subject are useful for the diagnosis and monitoring of certain medical conditions (e.g., metastatic cancer, infection with certain pathogenic agents).

16 Claims, 7 Drawing Sheets

Specification includes a Sequence Listing.

(56) References Cited

U.S. PATENT DOCUMENTS

| | | |
|---|---|---|
| 2002/0119490 A1 | 8/2002 | Aebersold et al. |
| 2003/0059952 A1 | 3/2003 | Chait et al. |
| 2004/0014652 A1* | 1/2004 | Trouet .................. A61K 47/65 424/1.41 |
| 2004/0091943 A1 | 5/2004 | Schneider |
| 2005/0107583 A1 | 5/2005 | Jiang et al. |
| 2005/0260695 A1 | 11/2005 | Fleming et al. |
| 2006/0008856 A1 | 1/2006 | Singh et al. |
| 2006/0257883 A1 | 11/2006 | Bjoraker et al. |
| 2006/0292631 A1 | 12/2006 | Broberg et al. |
| 2007/0010433 A1 | 1/2007 | Albrechtsen et al. |
| 2007/0048752 A1 | 3/2007 | Yan et al. |
| 2007/0207555 A1 | 9/2007 | Guerra et al. |
| 2008/0026480 A1 | 1/2008 | Guerra |
| 2008/0064607 A1 | 3/2008 | Yang |
| 2008/0095758 A1 | 4/2008 | Lee et al. |
| 2008/0113875 A1 | 5/2008 | Chaurand et al. |
| 2008/0213377 A1 | 9/2008 | Bhatia et al. |
| 2008/0226562 A1 | 9/2008 | Groves et al. |
| 2008/0241955 A1 | 10/2008 | Purkayastha et al. |
| 2008/0253960 A1 | 10/2008 | Zheng et al. |
| 2009/0016988 A1 | 1/2009 | Buckley |
| 2009/0088332 A1 | 4/2009 | Ju et al. |
| 2009/0156424 A1 | 6/2009 | Thompson |
| 2009/0230300 A1 | 9/2009 | Trevejo et al. |
| 2009/0246142 A1 | 10/2009 | Bhatia et al. |
| 2009/0252677 A1 | 10/2009 | Bogyo et al. |
| 2010/0022408 A1 | 1/2010 | Singh et al. |
| 2010/0124757 A1 | 5/2010 | Kwon et al. |
| 2010/0190193 A1 | 7/2010 | Calatzis et al. |
| 2010/0240050 A1* | 9/2010 | Bhatia .................. C12Q 1/37 435/6.14 |
| 2010/0317542 A1 | 12/2010 | Lim et al. |
| 2011/0014125 A1* | 1/2011 | Bossmann ............. C07K 7/06 424/9.1 |
| 2011/0021908 A1 | 1/2011 | Lee et al. |
| 2011/0104052 A1 | 5/2011 | Barnett et al. |
| 2011/0104071 A1 | 5/2011 | Lee et al. |
| 2012/0039990 A1 | 2/2012 | Reshetnyak et al. |
| 2012/0150164 A1 | 6/2012 | Lee et al. |
| 2013/0078188 A1 | 3/2013 | Tsien et al. |
| 2013/0295129 A1* | 11/2013 | Irvine ................ A61K 39/0011 424/194.1 |
| 2013/0315906 A1 | 11/2013 | Lowman et al. |
| 2014/0207129 A1 | 7/2014 | Lee |
| 2014/0234431 A1 | 8/2014 | Bhatia et al. |
| 2014/0255313 A1 | 9/2014 | Vasiljeva et al. |
| 2014/0276102 A1 | 9/2014 | Lee et al. |
| 2014/0276103 A1 | 9/2014 | Lee et al. |
| 2014/0301950 A1 | 10/2014 | Lee et al. |
| 2014/0303014 A1 | 10/2014 | Kwong et al. |
| 2014/0363833 A1 | 12/2014 | Bhatia et al. |
| 2014/0364368 A1 | 12/2014 | Lin et al. |
| 2015/0051153 A1 | 2/2015 | Reshetnyak et al. |
| 2015/0080721 A1 | 3/2015 | Novak et al. |
| 2015/0104381 A1 | 4/2015 | Maina-Nock et al. |
| 2015/0165062 A1 | 6/2015 | Liao et al. |
| 2015/0344523 A1 | 12/2015 | Deyle et al. |
| 2016/0025632 A1 | 1/2016 | Lee et al. |
| 2016/0096869 A1 | 4/2016 | Hansen et al. |
| 2016/0184459 A1 | 6/2016 | Ueki et al. |
| 2016/0289324 A1 | 10/2016 | Moore et al. |
| 2016/0317037 A1 | 11/2016 | Lee et al. |
| 2017/0267727 A1 | 9/2017 | Thevenin et al. |
| 2017/0305968 A1 | 10/2017 | Tsien et al. |
| 2018/0021090 A1 | 1/2018 | Lee et al. |
| 2018/0196058 A1 | 7/2018 | Kwong et al. |
| 2018/0328941 A1* | 11/2018 | Bhatia .................. G01N 33/6848 |
| 2018/0335429 A1 | 11/2018 | Bhatia et al. |
| 2019/0076081 A1 | 3/2019 | Hyde et al. |
| 2019/0144917 A1 | 5/2019 | Bhatia et al. |
| 2019/0212291 A1 | 7/2019 | Dudani et al. |
| 2019/0271704 A1 | 9/2019 | Bhatia et al. |
| 2019/0345534 A1 | 11/2019 | Kwong et al. |
| 2019/0376113 A1 | 12/2019 | Bhatia et al. |
| 2020/0096514 A1 | 3/2020 | Bhatia et al. |
| 2020/0116725 A1 | 4/2020 | Bhatia et al. |
| 2020/0225231 A1 | 7/2020 | Bhatia et al. |
| 2020/0232986 A1 | 7/2020 | Bhatia et al. |
| 2020/0249194 A9* | 8/2020 | Dudani .................. C12Q 1/005 |
| 2021/0148926 A1 | 5/2021 | Bhatia et al. |
| 2021/0262025 A1 | 8/2021 | Bhatia et al. |

FOREIGN PATENT DOCUMENTS

| | | |
|---|---|---|
| CN | 108484847 A | 9/2018 |
| JP | 2004-506900 | 3/2004 |
| JP | 2004-129651 | 4/2004 |
| JP | 2007-24631 A2 | 2/2007 |
| JP | 2007-206054 A | 8/2007 |
| JP | 2009-108037 | 5/2009 |
| JP | 2009-524688 | 7/2009 |
| JP | 2009-538430 A | 11/2009 |
| JP | 2013-060452 | 4/2013 |
| JP | 2016-520327 | 7/2016 |
| WO | WO 2002/014867 A2 | 2/2002 |
| WO | WO 2006/034370 A2 | 3/2006 |
| WO | WO 2007/060921 A1 | 5/2007 |
| WO | WO 2007/072070 A1 | 6/2007 |
| WO | WO 2008/072676 A1 | 6/2008 |
| WO | WO 2008/093513 A1 | 8/2008 |
| WO | WO 2008/127019 A1 | 10/2008 |
| WO | WO 2009/124265 A1 | 10/2009 |
| WO | WO 2010/101628 A2 | 9/2010 |
| WO | WO 2011/008996 A2 | 1/2011 |
| WO | WO 2012/031250 A2 | 3/2012 |
| WO | WO 2012/085080 A1 | 6/2012 |
| WO | WO 2012/125808 A1 | 9/2012 |
| WO | WO 2014/107599 A2 | 7/2014 |
| WO | WO 2014/120619 A2 | 8/2014 |
| WO | WO 2014/120974 A1 | 8/2014 |
| WO | WO 2014/176284 A1 | 10/2014 |
| WO | WO 2014/197816 | 12/2014 |
| WO | WO 2014/197840 A1 | 12/2014 |
| WO | WO 2015/042202 A1 | 3/2015 |
| WO | WO 2017/044894 A2 | 3/2017 |
| WO | WO 2017/120410 A1 | 7/2017 |
| WO | WO 2017/177115 A1 | 10/2017 |
| WO | WO 2017/180789 A2 | 10/2017 |
| WO | WO 2017/181149 A1 | 10/2017 |
| WO | WO 2018/049285 A1 | 3/2018 |
| WO | WO 2018/064383 A1 | 4/2018 |
| WO | WO 2018/187688 A1 | 10/2018 |
| WO | WO 2018/227132 A1 | 12/2018 |
| WO | WO 2019/071051 A1 | 4/2019 |
| WO | WO 2019/075292 A1 | 4/2019 |
| WO | WO 2019/089804 A1 | 5/2019 |
| WO | WO 2019/089820 A1 | 5/2019 |
| WO | WO 2019/126577 A2 | 6/2019 |
| WO | WO 2019/126716 A1 | 6/2019 |
| WO | WO 2019/126762 A2 | 6/2019 |
| WO | WO 2019/148206 A1 | 8/2019 |

OTHER PUBLICATIONS

Wu et al. 2014 (Expression and Clinical Significance of Matrix Metalloproteinase-9 in Lymphatic Invasiveness and Metastasis of Breast Cancer; PLOS One 9(5): e97804). (Year: 2014).*

Rosualova et al. 2010 Granzyme B-induced apoptosis in cancer cells and its regulation (Review); International Journal of Oncology 37:1361-1378). (Year: 2010).*

Abrahamson et al., Isolation of six cysteine proteinase inhibitors from human urine. Their physicochemical and enzyme kinetic properties and concentrations in biological fluids. J Biol Chem. Aug. 25, 1986;261(24):11282-9.

Abudayyeh, Nanoparticle-Chaperoned Urinary "Synthetic Biomarkers" for Profiling Proteases in Cancer. Thesis. Department of Mechanical Engineering. Jun. 2012.

Anderson et al., Mass spectrometric quantitation of peptides and proteins using Stable Isotope Standards and Capture by Anti-Peptide Antibodies (SISCAPA). J Proteome Res. Mar.-Apr. 2004;3(2):235-44.

(56) References Cited

OTHER PUBLICATIONS

Asai et al., A colorimetric assay for plasma antithrombin III using a new synthetic peptide substrate (PS-915). Clin Chim Acta. Dec. 29, 1984;144(2-3):163-71.
Baruch et al., Enzyme activity—it's all about image. Trends Cell Biol. Jan. 2004;14(1):29-35.
Becker et al., Thrombin: Structure, Biochemistry, Measurement, and Status in Clinical Medicine. J Thromb Thrombolysis. Jul. 1998;5(3):215-229.
Blum et al., Noninvasive optical imaging of cysteine protease activity using fluorescently quenched activity-based probes. Nat Chem Biol. Oct. 2007;3(10):668-77. Epub Sep. 9, 2007.
Böhm et al., uPA/PAI-1 ratios distinguish benign prostatic hyperplasia and prostate cancer. J Cancer Res Clin Oncol. Jul. 2013;139(7):1221-8. doi: 10.1007/s00432-013-1428-y. Epub Apr. 18, 2013.
Bounameaux et al., Plasma measurement of D-dimer as diagnostic aid in suspected venous thromboembolism: an overview. Thromb Haemost. Jan. 1994;71(1):1-6.
Chen et al., A unique substrate recognition profile for matrix metalloproteinase-2. J Biol Chem. Feb. 8, 2002;277(6):4485-91.
Daniel et al., Implantable diagnostic device for cancer monitoring. Biosens Bioelectron. Jul. 15, 2009;24(11):3252-7. Epub Apr. 16, 2009.
De La Rica et al., Enzyme-responsive nanoparticles for drug release and diagnostics. Adv Drug Deliv Rev. Aug. 2012;64(11):967-78. doi: 10.1016/j.addr.2012.01.002. Epub Jan. 14, 2012.
Deng et al., Gold nanoparticles based molecular beacons for in vitro and in vivo detection of the matriptase expression on tumor. Biosens Bioelectron. Nov. 15, 2013;49:216-21. doi: 10.1016/j.bios.2013.05.018. Epub May 25, 2013.
Dennis et al., Albumin binding as a general strategy for improving the pharmacokinetics ofproteins. J Biol Chem. Sep. 20, 2002;277(38):35035-43. Epub Jul. 15, 2002.
Deshpande et al., Current trends in the use of liposomes for tumor targeting. Nanomedicine (Lond). Sep. 2013;8(9):1509-28. doi:10.2217/nnm.13.118.
Dranoff, Cytokines in cancer pathogenesis and cancer therapy. Nat Rev Cancer. Jan. 2004;4(1):11-22.
D'Souza et al., A strategy for blood biomarker amplification and localization using ultrasound. Proc Natl Acad Sci U S A. Oct. 6, 2009;106(40):17152-7. doi: 10.1073/pnas.0903437106. Epub Sep. 23, 2009.
Dudani et al., Classification of prostate cancer using a protease activity nanosensor library. Proc Natl Acad Sci U S A. Sep. 4, 2018;115(36):8954-8959. doi: 10.1073/pnas.1805337115. Epub Aug. 20, 2018.
Dudani et al., Harnessing Protease Activity to Improve Cancer Care. Ann Rev Cancer Biol. Mar. 2018;2:353-376.
Dudani et al., Photoactivated Spatiotemporally-Responsive Nanosensors of in Vivo Protease Activity. ACS Nano. Dec. 22, 2015;9(12):11708-17. doi: 10.1021/acsnano.5b05946. Epub Nov. 13, 2015.
Dudani et al., Sustained-release synthetic biomarkers for monitoring thrombosis and inflammation using point-of-care compatible readouts. Adv Funct Mater. May 3, 2016;26(17):2919-2928. doi: 10.1002/adfm.201505142. Epub Mar. 22, 2016.
Farrell et al., Non-motor parkinsonian pathology in aging A53T α-synuclein mice is associated with progressive synucleinopathy and altered enzymatic function. J Neurochem. Feb. 2014;128(4):536-46. doi: 10.1111/jnc.12481. Epub Nov. 20, 2013.
Fowlkes et al., Proteolysis of insulin-like growth factor binding protein-3 during rat pregnancy: a role for matrix metalloproteinases. Endocrinology. Dec. 1994;135(6):2810-3.
Fusaro et al., Prediction of high-responding peptides for targeted protein assays by mass spectrometry. Nat Biotechnol. Feb. 2009;27(2):190-8. doi: 10.1038/nbt.1524. Epub Jan. 25, 2009.
Gartrell et al., Managing bone metastases and reducing skeletal related events in prostate cancer. Nat Rev Clin Oncol. Jun. 2014;11(6):335-45. doi: 10.1038/nrclinonc.2014.70. Epub May 13, 2014. Review. Erratum in: Nat Rev Clin Oncol. Jan. 2015;12(1). doi:10.1038/nrclinonc.2014.70.

Genbank Submission; NIH/NCBI, Accession No. 2WV1_A; Kovalevskiy et al.; Mar. 24, 2010.
Genbank Submission; NIH/NCBI, Accession No. CAG01641; Mar. 17, 2004.
Genbank Submission; NIH/NCBI, Accession No. NP_731669; Hoskins et al.; Dec. 18, 2009.
Genbank Submission; NIH/NCBI, Accession No. NP_938673; Cerdeno-Tarraga et al.; Jun. 3, 2010.
Genbank Submission; NIH/NCBI, Accession No. XP_001385378; Jeffries et al.; Apr. 11, 2008.
Genbank Submission; NIH/NCBI, Accession No. XP_002097000; Clark et al.; Aug. 12, 2009.
Genbank Submission; NIH/NCBI, Accession No. XP_0234527.; Jul. 7, 2006.
Genbank Submission; NIH/NCBI, Accession No. ZP_03507634; Gonzalez et al.; Dec. 19, 2008.
Genbank Submission; NIH/NCBI, Accession No. ZP_06431346; Small et al.; Jun. 9, 2010.
Ghadiali, James E. et al., "Enzyme-Responsive Nanoparticle Systems," Advanced Materials, vol. 20(22):4359-4363 (2008).
Giljohann, et al., Drivers of biodiagnostic development. Nature. Nov. 26, 2009;462(7272):461-4. doi: 10.1038/nature08605.
Ginsberg et al., Sensitivity and specificity of a rapid whole-blood assay for D-dimer in the diagnosis of pulmonary embolism. Ann Intern Med. Dec. 15, 1998; 129(12):1006-11.
Grayson et al., Multi-pulse drug delivery from a resorbable polymeric microchip device. Nat Mater. Nov. 2003;2(11):767-72.
Gross, Mass Spectrometry: A Textbook. Springer. $2^{nd}$ ed. Mar. 1, 2011. Chapter 9. 415-452.
Haro et al., Matrix metalloproteinase-7-dependent release of tumor necrosis factor-alpha in a model of herniated disc resorption. J Clin Invest. Jan. 2000;105(2):143-50.
Haun et al., Micro-NMR for rapid molecular analysis of human tumor samples. Sci Transl Med. Feb. 23, 2011;3(71):71ra16. doi: 10.1126/scitranslmed.3002048.
Imai et al., Degradation of decorin by matrix metalloproteinases: identification of the cleavage sites, kinetic analyses and transforming growth factor-beta1 release. Biochem J. Mar. 15, 1997;322 (Pt 3):809-14.
Ito et al., Degradation of interleukin 1beta by matrix metalloproteinases. J Biol Chem. Jun. 21, 1996;271(25):14657-60.
Jaffer et al., In vivo imaging of thrombin activity in experimental thrombi with thrombin-sensitive near-infrared molecular probe. Arterioscler Thromb Vasc Biol. Nov. 1, 2002;22(11):1929-35.
Johnson et al., Computer program (SEQPEP) to aid in the interpretation of high-energy collision tandem mass spectra of peptides. Biomed Environ Mass Spectrom. Nov. 1989;18(11):945-57.
Kaminskas et al., Methotrexate-conjugated PEGylated dendrimers show differential patterns of deposition and activity in tumor-burdened lymph nodes after intravenous and subcutaneous administration in rats. Mol Pharm. Feb. 2, 2015;12(2):432-43. doi: 10.1021/mp500531e. Epub Jan. 20, 2015.
Kastelic et al., Stefin B, the major low molecular weight inhibitor in ovarian carcinoma. Cancer Lett. Jul. 15, 1994;82(1):81-8.
Kircher et al., A dual fluorochrome probe for imaging proteases. Bioconjug Chem. Mar.-Apr. 2004;15(2):242-8.
Klotz et al., Management of low risk prostate cancer-active surveillance and focal therapy. Nat Rev Clin Oncol. Jun. 2014;11(6):324-34. doi: 10.1038/nrclinonc.2014.73. Epub May 13, 2014.
Ku et al., In vivo sensing of proteolytic activity with an NSET-based NIR fluorogenic nanosensor. Biosens Bioelectron. Mar. 15, 2016;77:471-7. doi: 10.1016/j.bios.2015.09.067. Epub Sep. 30, 2015.
Kuhn et al., Developing multiplexed assays for troponin I and interleukin-33 in plasma by peptide immunoaffinity enrichment and targeted mass spectrometry. Clin Chem. Jun. 2009;55(6):1108-17. doi: 10.1373/clinchem.2009.123935. Epub Apr. 16, 2009.
Kwon et al., Ultrasensitive tumour-penetrating nanosensors of protease activity. Nat Biomed Eng. 2017;1. pii: 0054. doi:10.1038/s41551-017-0054. Epub Apr. 10, 2017.
Kwong et al., Mass-encoded synthetic biomarkers for multiplexed urinary monitoring of disease. Nat Biotechnol. Jan. 2013;31(1):63-70. doi: 10.1038/nbt.2464. Epub Dec. 16, 2012.

(56) References Cited

OTHER PUBLICATIONS

Kwong et al., Mathematical framework for activity-based cancer biomarkers. Proc Natl Acad Sci U S A. Oct. 13, 2015; 112(41):12627-32. doi: 10.1073/pnas.1506925112. Epub Sep. 28, 2015.

Lange et al., Selected reaction monitoring for quantitative proteomics: a tutorial. Mol Syst Biol. 2008;4:222. doi: 10.1038/msb.2008.61. Epub Oct. 14, 2008.

Larsen et al., Assay of plasma heparin using thrombin and the chromogenic substrate H-D-Phe-Pip-Arg-pNA (S-2238). Thromb Res. Aug. 1978;13(2):285-8.

Lebeau et al., Imaging active urokinase plasminogen activator in prostate cancer. Cancer Res. Apr. 1, 2015;75(7):1225-35. doi:10.1158/0008-5472.CAN-14-2185. Epub Feb. 11, 2015.

Levi et al., Matrix metalloproteinase 2 releases active soluble ectodomain of fibroblast growth factor receptor 1. Proc Natl Acad Sci U S A. Jul. 9, 1996;93(14):7069-74.

Lin et al., Drug-induced amplification of nanoparticle targeting to tumors. Nano Today. Oct. 2014;9(5):550-559. doi:10.1016/j.nantod.2014.09.001. Epub Sep. 23, 2014.

Lin et al., Nanoparticles that sense thrombin activity as synthetic urinary biomarkers of thrombosis. ACS Nano. Oct. 22, 2013;7(10):9001-9. doi: 10.1021/nn403550c. Epub Sep. 12, 2013.

Mallick et al., Computational prediction of proteotypic peptides for quantitative proteomics. Nat Biotechnol. Jan. 2007;25(1):125-31. Epub Dec. 31, 2006.

Mañes et al., The matrix metalloproteinase-9 regulates the insulin-like growth factor-triggered autocrine response in DU-145 carcinoma cells. J Biol Chem. Mar. 12, 1999;274(11):6935-45.

Martinez et al., Diagnostics for the developing world: microfluidic paper-based analytical devices. Anal Chem. Jan. 1, 2010;82(1):3-10. doi: 10.1021/ac9013989.

McLennan et al., Subcutaneous drug delivery and the role of the lymphatics. Drug Discov Today Technol. 2005 Spring;2(1):89-96. doi:10.1016/j.ddtec.2005.05.006.

Mira et al., Insulin-like growth factor I-triggered cell migration and invasion are mediated by matrix metalloproteinase-9. Endocrinology. Apr. 1999;140(4):1657-64.

Mirtti et al., Expression of cystatins, high molecular weight cytokeratin, and proliferation markers in prostatic adenocarcinoma and hyperplasia. Prostate. Mar. 1, 2003;54(4):290-8.

Mitchell et al., Assay for plasma heparin using a synthetic peptide substrate for thrombin: introduction of the fluorophore aminoisophthalic acid, dimethyl ester. Thromb Res. Jul. 1978;13(1):47-52.

Morgia et al., Matrix metalloproteinases as diagnostic (MMP-13) and prognostic (MMP-2, MMP-9) markers of prostate cancer. Urol Res. Feb. 2005;33(1):44-50. Epub Oct. 22, 2004.

Morris et al., Urine and plasma levels of fibrinopeptide B in patients with deep vein thrombosis and pulmonary embolism. Thromb Res. May 1, 2003;110(2-3):159-65.

Nagase et al., Matrix metalloproteinases. J Biol Chem. Jul. 30, 1999;274(31):21491-4.

Nahrendorf et al., Hybrid in vivo FMT-CT imaging of protease activity in atherosclerosis with customized nanosensors. Arterioscler Thromb Vasc Biol. Oct. 2009;29(10):1444-51. doi:10.1161/ATVBAHA.109.193086. Epub Jul. 16, 2009. Supplemental Material.

Nomura et al., Activity-based protein profiling for biochemical pathway discovery in cancer. Nat Rev Cancer. Sep. 2010;10(9):630-8. doi: 10.1038/nrc2901. Epub Aug. 12, 2010.

Olson et al., In vivo fluorescence imaging of atherosclerotic plaques with activatable cell-penetrating peptides targeting thrombin activity. Integr Biol (Camb). Jun. 2012;4(6):595-605. doi: 10.1039/c2ib00161f. Epub Apr. 26, 2012.

Park et al., Magnetic Iron Oxide Nanoworms for Tumor Targeting and Imaging. Adv Mater. May 5, 2008;20(9):1630-1635.

Park et al., Systematic surface engineering of magnetic nanoworms for in vivo tumor targeting. Small. Mar. 2009;5(6):694-700. doi: 10.1002/smll.200801789.

Peer et al., Nanocarriers as an emerging platform for cancer therapy. Nat Nanotechnol. Dec. 2007;2(12):751-60.

Pomerantz et al., Determination of oligonucleotide composition from mass spectrometrically measured molecular weight. J Am Soc Mass Spectrom. Mar. 1993;4(3):204-9. doi: 10.1016/1044-0305(93)85082-9.

Posthuma-Trumpie et al., Lateral flow (immuno)assay: its strengths, weaknesses, opportunities and threats. A literature survey. Anal Bioanal Chem. Jan. 2009;393(2):569-82. doi: 10.1007/s00216-008-2287-2. Epub Aug. 13, 2008.

Powell et al., The metalloproteinase matrilysin proteolytically generates active soluble Fas ligand and potentiates epithelial cell apoptosis. Curr Biol. Dec. 16-30, 1999;9(24):1441-7.

Prensner et al., Beyond PSA: the next generation of prostate cancer biomarkers. Sci Transl Med. Mar. 28, 2012;4(127):127rv3. doi:10.1126/scitranslmed.3003180.

Rajah et al., Elevated levels of the IGF-binding protein protease MMP-1 in asthmatic airway smooth muscle. Am J Respir Cell Mol Biol. Feb. 1999;20(2):199-208.

Rennke, How does glomerular epithelial cell injury contribute to progressive glomerular damage? Kidney Int Suppl. Feb. 1994;45:S58-63.

Rijkers et al., Design and synthesis of thrombin substrates with modified kinetic parameters. Thromb Res. Sep. 15, 1995;79(5-6):491-9.

Roepstorff et al., Proposal for a common nomenclature for sequence ions in mass spectra of peptides. Biomed Mass Spectrom. Nov. 1984;11(11):601.

Ross et al., Multiplexed protein quantitation in *Saccharomyces cerevisiae* using amine-reactive isobaric tagging reagents. Mol Cell Proteomics. Dec. 2004;3(12):1154-69. Epub Sep. 22, 2004.

Ruoslahti et al., Targeting of drugs and nanoparticles to tumors. J Cell Biol. Mar. 22, 2010;188(6):759-68. doi: 10.1083/jcb.200910104. Epub Mar. 15, 2010.

Santini et al., A controlled-release microchip. Nature. Jan. 28, 1999;397(6717):335-8.

Sawyers, The cancer biomarker problem. Nature. Apr. 3, 2008;452(7187):548-52. doi: 10.1038/nature06913.

Schonbeck et al., Generation of biologically active IL-1 beta by matrix metalloproteinases: a novel caspase-1-independent pathway of IL-1 beta processing. J Immunol. Oct. 1, 1998;161(7):3340-6.

Schuerle et al., Magnetically Actuated Protease Sensors for in Vivo Tumor Profiling. Nano Lett. Oct. 12, 2016;16(10):6303-6310. Epub Sep. 13, 2016.

Shariat et al., Urine detection of survivin is a sensitive marker for the noninvasive diagnosis of bladder cancer. J Urol. Feb. 2004;171(2 Pt 1):626-30.

Smith et al., Rapid identification of highly active and selective substrates for stromelysin and matrilysin using bacteriophage peptide display libraries. J Biol Chem. Mar. 24, 1995;270(12):6440-9

Stein et al., Ultrasensitive Scaffold-Dependent Protease Sensors with Large Dynamic Range. ACS Synth Biol. Jul. 21, 2017;6(7):1337-1342. doi: 10.1021/acssynbio.6b00370. Epub Mar. 28, 2017.

Sugahara et al., Coadministration of a tumor-penetrating peptide enhances the efficacy of cancer drugs. Science. May 21, 2010;328(5981):1031-5. doi:10.1126/science.1183057. Epub Apr. 8, 2010.

Sutherland et al., RGD-Binding Integrins in Prostate Cancer: Expression Patterns and Therapeutic Prospects against Bone Metastasis. Cancers (Basel). Oct. 26, 2012;4(4):1106-45. doi:10.3390/cancers4041106.

Suzuki et al., Matrix metalloproteinase-3 releases active heparin-binding EGF-like growth factor by cleavage at a specific juxtamembrane site. J Biol Chem. Dec. 12, 1997;272(50):31730-7.

Tascilar et al., Role of tumor markers and mutations in cells and pancreatic juice in the diagnosis of pancreatic cancer. Ann Oncol. 1999;10 Suppl 4:107-10.

Taylor et al., Integrative genomic profiling of human prostate cancer. Cancer Cell. Jul. 13, 2010;18(1):11-22. doi:10.1016/j.ccr.2010.05.026. Epub Jun. 24, 2010.

Thompson et al., Tandem mass tags: a novel quantification strategy for comparative analysis of complex protein mixtures by MS/MS. Anal Chem. Apr. 15, 2003;75(8):1895-904. Erratum in: Anal Chem. Sep. 15, 2003;75(18):4942. Johnstone, R [added]. Anal Chem. Jun. 15, 2006;78(12):4235. Mohammed, A Karim A [added].

(56) References Cited

OTHER PUBLICATIONS

Thorek et al., Internalization of secreted antigen-targeted antibodies by the neonatal Fc receptor for precision imaging of the androgen receptor axis. Sci Transl Med. Nov. 30, 2016;8(367):367ra167.

Tockman et al., Considerations in bringing a cancer biomarker to clinical application. Cancer Res. May 1, 1992;52(9 Suppl):2711s-2718s.

Traxlmayr et al., Strong Enrichment of Aromatic Residues in Binding Sites from a Charge-neutralized Hyperthermostable Sso7d Scaffold Library. J Biol Chem. Oct. 21, 2016;291(43):22496-22508. Epub Aug. 30, 2016.

Truong et al., Isotope-coded chemical reporter and acid-cleavable affinity reagents for monitoring protein sulfenic acids. Bioorg Med Chem Lett. Sep. 1, 2011;21(17):5015-20. doi: 10.1016/j.bmcl.2011. 04.115. Epub May 3, 2011.

Tung et al., A novel near-infrared fluorescence sensor for detection of thrombin activation in blood. Chembiochem. Mar. 1, 2002;3(2-3):207-11.

Warren et al., Point-of-care diagnostics for noncommunicable diseases using synthetic urinary biomarkers and paper microfluidics. Proc Natl Acad Sci U S A. Mar. 11, 2014;111(10):3671-6. doi:10. 1073/pnas.1314651111. Epub Feb. 24, 2014.

Weissleder et al., In vivo imaging of tumors with protease-activated near-infrared fluorescent probes. Nat Biotechnol. Apr. 1999;17(4):375-8.

Welser et al., Protease responsive nanoprobes with tethered fluorogenic peptidyl 3-arylcoumarin substrates. Chem Commun (Camb). Feb. 14, 2009;(6):671-3. Epub Dec. 8, 2008.

Welser et al., Protease sensing with nanoparticle based platforms. Analyst. Jan. 7, 2011;136(1):29-41. doi: 10.1039/c0an00429d. Epub Sep. 22, 2010.

Whiteaker et al., An automated and multiplexed method for high throughput peptide immunoaffinity enrichment and multiple reaction monitoring mass spectrometry-based quantification of protein biomarkers. Mol Cell Proteomics. Jan. 2010;9(1):184-96. doi: 10.1074/mcp.M900254-MCP200. Epub Oct. 20, 2009.

Whiteaker et al., Antibody-based enrichment of peptides on magnetic beads for mass-spectrometry-based quantification of serum biomarkers. Anal Biochem. Mar. 1, 2007;362(1):44-54. Epub Dec. 20, 2006.

Whitney et al., Ratiometric activatable cell-penetrating peptides provide rapid in vivo readout of thrombin activation. Angew Chem Int Ed Engl. Jan. 2, 2013;52(1):325-30. doi: 10.1002/anie. 201205721. Epub Oct. 18, 2012.

Withana et al., Labeling of active proteases in fresh-frozen tissues by topical application of quenched activity-based probes. Nat Protoc. Jan. 2016;11(1):184-91. doi: 10.1038/nprot.2016.004. Epub Dec. 30, 2015.

Wollscheid et al., Mass-spectrometric identification and relative quantification of N-linked cell surface glycoproteins. Nat Biotechnol. Apr. 2009;27(4):378-86. doi: 10.1038/nbt.1532. Epub Apr. 6, 2009. Erratum in: Nat Biotechnol. Sep. 2009;27(9):864.

Xia et al., Multiplex detection of protease activity with quantum dot nanosensors prepared by Intein-Mediated specific bioconjugation. Analytical Chemistry. Nov. 15, 2008; 22(80) 8649-8655.

Yager et al., Point-of-care diagnostics for global health. Annu Rev Biomed Eng. 2008;10:107-44. doi: 10.1146/annurev.bioeng.10. 061807.160524.

Yu et al., Cell surface-localized matrix metalloproteinase-9 proteolytically activates TGF-beta and promotes tumor invasion and angiogenesis. Genes Dev. Jan. 15, 2000;14(2):163-76.

Zhang et al., Identification and quantification of N-linked glycoproteins using hydrazide chemistry, stable isotope labeling and mass spectrometry. Nat Biotechnol. Jun. 2003;21(6):660-6. Epub May 18, 2003.

Zieske, A perspective on the use of iTRAQ reagent technology for protein complex and profiling studies. J Exp Bot. 2006;57(7):1501-8. Epub Mar. 30, 2006.

U.S. Appl. No. 15/966,385, filed Apr. 30, 2018, Bhatia et al.
U.S. Appl. No. 15/842,162, filed Dec. 14, 2017, Kwong et al.
U.S. Appl. No. 16/691,788, filed Nov. 22, 2019, Bhatia et al.
U.S. Appl. No. 16/099,147, filed Nov. 5, 2018, Bhatia et al.
U.S. Appl. No. 15/947,644, filed Apr. 5, 2018, Bhatia et al.
U.S. Appl. No. 16/159,340, filed Oct. 12, 2018, Dudani et al.
U.S. Appl. No. 16/293,390, filed Mar. 5, 2019, Bhatia et al.
U.S. Appl. No. 16/582,053, filed Sep. 25, 2019, Bhatia et al.
U.S. Appl. No. 16/745,748, filed Jan. 17, 2020, Bhatia et al.
U.S. Appl. No. 16/654,572, filed Oct. 16, 2019, Bhatia et al.
PCT/US2017/026564, Aug. 16, 2017, International Search Report and Written Opinion.
PCT/US2017/026564, Jun. 23, 2017, Invitation to Pay Additional Fees.
PCT/US2017/026564, Oct. 18, 2018, International Preliminary Report on Patentability.

Aalipour et al., Engineered immune cells as highly sensitive cancer diagnostics. Nat Biotechnol. 2019;37:531-9.

Acharige et al., Breath-based diagnosis of fungal infections. J Breath Res. Feb. 6, 2018;12(2):027108. doi: 10.1088/1752-7163/aa98a1.

Amstad et al., Photo- and thermoresponsive polymersomes for triggered release. Angew Chem Int Ed. 2012;51:1-6.

Beauchamp et al., Real-time breath gas analysis for pharmacokinetics: monitoring exhaled breath by on-line proton-transfer-reaction mass spectrometry after ingestion of eucalyptol-containing capsules. J Breath Res. Jun. 2010;4(2):026006. doi: 10.1088/1752-7155/4/2/026006. Epub Apr. 22, 2010.

Bartlett, Diagnostic tests for agents of community-acquired pneumonia. Clin Infect Dis. May 2011. 52(Suppl 4):S296-304. doi: 10.1093/cid/cir045.

Bascom et al., Use of Enzyme Tests in Characterization and Identification of Aerobic and Facultatively Anaerobic Gram-Positive Cocci. Clin Microbiol Rev. Apr. 1998; 11(2): 318-340.

Berger, Helicobacter pylori breath tests. BMJ. 2002;324:1263.

Bonomi et al., Detection of enzyme activity through catalytic signal amplification with functionalized gold nanoparticles. Angew Chem Int Ed. 2011;50:2307-12.

Buss et al., Protease activity sensors noninvasively classify bacterial infections and antibiotic responses. EBioMedicine. Dec. 2018;38:248-56. doi:10.1016/j.ebiom.2018.11.031.

Caliendo et al., Better Tests, Better Care: Improved Diagnostics for Infectious Diseases. Clin Infect Dis. Dec. 2013;57(3):S139-S170.

Castillo et al., Sensitive substrates for human leukocyte and porcine pancreatic elastase: A study of the merits of various chromophoric and fluorogenic leaving groups in assays for serine proteases. Anal Biochem. Oct. 1979;99(1):53-64.

Chan et al., Inhalable Nanosensors for Rapid Breath-Based Pathogen Identification in Respiratory Infection. Revolutions in Biotechnology. MIT. Presented Mar. 5-6, 2018 at Tang Center, MIT Campus. 1 page.

Cheng et al., Ultrasensitive scanometric strategy for detection of matrix metalloproteinases using a histidine tagged peptide—Au nanoparticle probe. Chem Commun. 2011;47:2877-9.

Coelho et al., Usefulness of C-reactive protein in monitoring the severe community-acquired pneumonia clinical course. Crit Care. Aug. 2007; 11(4):R92.

Cohen et al., Detection and localization of surgically resectable cancers with a multi-analyte blood test. Science. 2018;3247(80):1-10.

El Badrawy et al., Matrix Metalloproteinase-9 Expression in Lung Cancer Patients and Its Relation to Serum MMP-9 Activity, Pathologic Type, and Prognosis. J Bronchol Interven Pulmonol. Oct. 2014; 21(4):327-34. doi: 10.1097/LBR.0000000000000094.

Elegbede et al., Mechanistic studies of the triggered release of liposomal contents by matrix metalloproteinase-9. J Am Chem Soc. Aug. 13, 2008;130(32):10633-42. doi: 10.1021/ja801548g. Epub Jul. 22, 2008.

Elston et al., New continuous and specific fluorometric assays for Pseudomonas aeruginosa elastase and LasA protease. Anal Biochem. Sep. 2007;368(1):87-94.

Fernandez et al., Volatile Biomarkers in Breath Associated With Liver Cirrhosis—Comparisons of Pre- and Post-liver Transplant Breath Samples. EBIOM. 2015;2:1243-50.

(56) References Cited

OTHER PUBLICATIONS

Figueiredo et al., Near infrared thoracoscopy of tumoral protease activity for improved detection of peripheral lung cancer. Int J Cancer. Jun. 2006;118(11):2672-7. doi: 10.1002/ijc.21713.

Gaieska et al., Impact of time to antibiotics on survival in patients with severe sepsis or septic shock in whom early goal-directed therapy was initiated in the emergency department. Crit Care Med. Apr. 2010;38(4):1045-53. doi: 10.1097/CCM.0b013e3181cc4824.

Ghoshal et al., How to Interpret Hydrogen Breath Tests. J Neurogastroenterol Motil. 2011;17:312-7.

Haiko et al., The omptins of *Yersinia pestis* and *Salmonella enterica* cleave the reactive center loop of plasminogen activator inhibitor 1. J Bacteriol. Sep. 2010;192(18):4553-61. doi: 10.1128/JB.00458-10. Epub Jul. 16, 2010.

Harris et al., Protease-triggered unveiling of bioactive nanoparticles. Small. 2008;4(9):1307-12. doi: 10.1002/smll.200701319. Epub Aug. 8, 2008.

Haskins, The application of stable isotopes in biomedical research. Biomed Mass Spectrom. Jul. 1982;9(7):269-77.

Heaney et al., Real-time monitoring of exhaled volatiles using atmospheric pressure chemical ionization on a compact mass spectrometer. Bioanalysis. Jul. 2016;8(13):1325-36. doi: 10.4155/bio-2016-0045. Epub Jun. 9, 2016.

Herbig et al., Towards standardization in the analysis of breath gas volatiles. J Breath Res. 2014;8:1-11.

Holliday et al., Rapid Identification of *Staphylococcus aureus* by Using Fluorescent Staphylocoagulase Assays. J Clin Microbiol. Apr. 1999;37(4):1190-2.

Iwasaki et al., Control of adaptive immunity by the innate immune system. Nat Immunol. Mar. 19, 2015;16(4):343-53.

Janzen et al., Colorimetric sensor arrays for volatile organic compounds. Anal Chem. Jun. 1, 2006;78(11):3591-600.

Johnson et al., Active-site gating regulates substrate selectivity in a chymotrypsin-like serine protease the structure of haemophilus influenzae immunoglobulin A1 protease. J Mol Biol. Jun. 12, 2009;389(3):559-74. doi: 10.1016/j.jmb.2009.04.041. Epub Apr. 23, 2009.

Kalinska et al., Substrate specificity of *Staphylococcus aureus* cysteine proteases—Staphopains A, B and C. Biochimie. Feb. 2012;94(2):318-27. doi: 10.1016/j.biochi.2011.07.020. Epub Jul. 23, 2011.

Kaman et al., Evaluation of a FRET-Peptide Substrate to Predict Virulence in Pseudomonas aeruginosa. PLoS One; Nov. 2013;8(11):e81428.

Kasperkiewicz et al., Design of ultrasensitive probes for human neutrophil elastase through hybrid combinatorial substrate library profiling. PNAS. 2014;111:2518-23.

Kim et al., Applications of stable, nonradioactive isotope tracers in in vivo human metabolic research. Exp Mol Med. Jan. 2016; 48(1): e203. Epub Jan. 15, 2016. doi: 10.1038/emm.2015.97.

Kirkpatrick et al., Noninvasive lung cancer detection via pulmonary protease profiling. bioRxiv. 36 pages, doi: https://doi.org/10.1101/495259.

Krebs et al., Molecular analysis of circulating tumour cells-biology and biomarkers. Nat Rev Clin Oncol. 2014;11:129-44.

Krilaviciute et al., Detection of cancer through exhaled breath?: a systematic review Literature search. Oncotarget. 2015;6:38643-57.

Kulkarni et al., MMP-9 Responsive PEG Cleavable Nanovesicles for Efficient Delivery of Chemotherapeutics to Pancreatic Cancer. Mol Pharm. Jul. 7, 2014; 11(7): 2390-2399. doi: 10.1021/mp500108p.

Kwak et al., Volatile disease biomarkers in breath: a critique. Curr Pharm Biotechnol; 2011;12:1067-74.

Kwon et al., Porous Silicon Nanoparticle Delivery of Tandem Peptide Anti Infectives for the Treatment of Pseudomonas aeruginosa Lung Infections. Adv Mat. Sep. 20, 2017;29(35). 21pages.

Laupland et al., The changing culture of the microbiology laboratory. Can J Infect Dis Med Microbiol. 2013 Autumn; 24(3):125-128. doi: 10.1155/2013/101630.

Liou et al., Nonisotropic Enzyme-Inhibitor Interactions: A Novel Nonoxidative Mechanism for Quantum Proteolysis by Human Neutrophils. Biochem. 1995;34(49):16171-7.

Loynachan et al., ANYL 234: Catalytic nanomaterials for amplified biosensing. Abstract of Papers, 256th National Meeting & Exposition of the ACS. ACS National Meeting & Exposition. Aug. 19, 2018. 1 page.

Matsumoto et al., Role of bacterial proteases in pseudomonal and serratial keratitis. Biol Chem. Jan. 2004;385(11):1007-16.

McCarter et al., Substrate Specificity of the *Escherichia coli* Outer Membrane Protease OmpT. J Bacteriol. Sep. 2004; 186(17): 5919-5925. doi: 10.1128/JB.186.17.5919-5925.2004.

Meyer et al., Respiratory protease / antiprotease balance determines susceptibility to viral infection and can be modified by nutritional antioxidants. Am J Physiol Lung Cell Mol Physiol. 2015;308:L1189-L1201.

Morihara, Pseudolysin and other pathogen endopeptidases of thermolysin family. Methods in Enzymol. 1995;248:242-53.

Murray, What Is New in Clinical Microbiology—Microbial Identification by MALDI-TOF Mass Spectrometry. JMDI. 2012;14:419-23.

Nizio et al., In vitro volatile organic compound profiling using GCxGC-TOFMS to differentiate bacteria associated with lung infections: a proof-of-concept study. J Breath Res. Apr. 27, 2016;10:026008, 12 pages.

Ong et al., Inhalable nanosensors for rapid breath-based pathogen identification in respiratory infection. Adv Res Technol Symp. Mar. 5, 2018. 2 pages.

Ong et al., Use of Mass Spectrometric Vapor Analysis to Improve Canine Explosive Detection Efficiency. Anal Chem. 2017;89:6482-90.

Parks et al., Matrix metalloproteinases as modulators of inflammation and innate immunity. Nat Rev Immunol. Aug. 2004;4(8):617-29.

Patton et al., Inhaling medicines: delivering drugs to the body through the lungs. Nat Rev Drug Discov. Jan. 2007;6(1):67-74.

Patton et al., The lungs as a portal of entry for systemic drug delivery. Proc Am Thorac Soc. 2004;1(4):338-44.

Phillips et al., Variation in volatile organic compounds in the breath of normal humans. J Chromatogr B. 1999;729:75-88.

Potempa et al., Corruption of innate immunity by bacterial proteases. J Innate Immun. 2009;1(2):70-87.

Ross et al., Volatile compounds in blood headspace and nasal breath. J Breath Res. Sep. 13, 2017;11(4):046001. doi: 10.1088/1752-7163/aa7d10.

Roy et al., Matrix metalloproteinases as novel biomarkers and potential therapeutic targets in human cancer. J Clin Oncol. 2009;27:5287-97.

Sethi et al., Clinical application of volatile organic compound analysis for detecting infectious diseases. Clin Microbiol Rev. Jul. 2013;26(3):462-75. doi: 10.1128/CMR.00020-13.

Shaw et al., The role and regulation of the extracellular proteases of *Staphylococcus aureus*. Microbiol. Jan. 2004;150:217-28. doi: 10.1099/mic.0.26634-0.

Shibuya et al., Pseudomonas aeruginosa alkaline proteinase might share a biological function with plasmin. Biochim Biophys Acta. Apr. 29, 1991; 1077(3):316-24.

Stach et al., Unique Substrate Specificity of SplE Serine Protease from *Staphylococcus aureus*. Structure. Apr. 3, 2018;26(4):572-579.e4. doi: 10.1016/j.str.2018.02.008. Epub Mar. 8, 2018.

Sweeney et al., Robust classification of bacterial and viral infections via integrated host gene expression diagnostics. Sci Transl Med. Jul. 2016;8(346):346ra91.

Thomassin et al., OmpT Outer Membrane Proteases of Enterohemorrhagic and Enteropathogenic *Escherichia coli* Contribute Differently to the Degradation of Human LL-37. Infect Immun. Feb. 2012; 80(2): 483-492. doi: 10.1128/IAI.05674-11.

Van Der Schee et al., Breathomics in lung disease. Chest. 2015;147:224-31.

Vessillier et al., Hydrolysis of glycine-containing elastin pentapeptides by LasA, a metalloelastase from Pseudomonas aeruginosa. Eur J Biochem. Feb. 2001;268(4):1049-57.

(56) References Cited

OTHER PUBLICATIONS

Wang et al., Intrinsic enzyme mimicking activity of gold nanoclusters upon visible light triggering and its application for colorimetric trypsin detection. Biosens Bioelectronics. 2015;64:523-9. Epub Sep. 30, 2014.

Warren et al., Disease detection by ultrasensitive quantification of microdosed synthetic urinary biomarkers. J Am Chem Soc. 2014;136:13709-14.

Warren et al., Harnessing protease activity to improve cancer care. Annual Rev Cancer Biol. 2018;2:353-76.

Wildeboer et al., Characterization of bacterial proteases with a panel of fluorescent peptide substrates. Anal Biochem. Jan. 15, 2009;384(2):321-8. doi: 10.1016/j.ab.2008.10.004. Epub Oct. 11, 2008.

Wilkinson et al., Ventilator-Associated Pneumonia Is Characterized by Excessive Release of Neutrophil Proteases in the Lung. Chest. Dec. 2012;142(6): 1425-32.

Wilson et al., Applications and Advances in Electronic-Nose Technologies. Sensors (Basel). 2009;9(7):5099-148. doi: 10.3390/s90705099. Epub Jun. 29, 2009.

Zheng et al., Dual-reaction triggered sensitivity amplification for ultrasensitive peptide-cleavage based electrochemical detection of matrix metalloproteinase-7. Biosens Bioelectronics. 2018;103:46-52. Epub Feb. 21, 2018.

Zhou et al., Thermo-sensitive microgels supported gold nanoparticles as temperature-mediated catalyst. Chinese J Polym Sci. 2019;37:235-42. Epub Aug. 30, 2018.

Zhu et al., Detecting bacterial lung infections: in vivo evaluation of in vitro volatile fingerprints. J Breath Res. Jan. 10, 2013;7(1):016003, 7 pages.

Zumla et al., Rapid point of care diagnostic tests for viral and bacterial respiratory tract infections—needs, advances, and future prospects. Lancet Infect Dis. 2014;14(11):1123-35.

EP 17779900.4, Nov. 12, 2020, Supplementary Partial European Search Report.

Supplementary Partial European Search Report dated Nov. 12, 2020 for Application No. EP 17779900.4.

[No Author Listed] Summary for peptidase S01.135: granzyme A. MEROPS. Retrieved from <https://www.ebi.ac.uk/merops/cgi-bin/pepsum?id=S01.135;type=P>. Apr. 26, 2019. 2 pages.

[No Author Listed] Summary for peptidase S01.010: granzyme B. MEROPS. Retrieved from <https://www.ebi.ac.uk/merops/cgi-bin/pepsum?id=S01.010;type=P>. Apr. 26, 2019. 2 pages.

[No Author Listed] Summary for peptidase S01.146: granzyme K. MEROPS. Retrieved from <https://www.ebi.ac.uk/merops/cgi-bin/pepsum?id=S01.146;type=P>. Apr. 26, 2019. 2 pages.

[No Author Listed], DQ™ Gelatin From Pig Skin, Fluorescein Conjugate—Special Packaging. ThermoFisher Scientific. ENZCHEK® Gelatinase/Collagenase Assay Kit Product Information Sheet. Accessed on Jul. 14, 2020. Retrieved from: <https://www.thermofisher.com/order/catalog/product/D12054#/D12054>. 4 pages.

Chan et al., Engineering synthetic breath biomarkers for respiratory disease. Nature Nanotechnol. Jul. 20, 2020;15:792-800.

Cheng et al., Multifunctional nanoparticles: Cost versus benefit of adding targeting and imaging capabilities. Sci. Nov. 16, 2012;338(6109):903-10.

Galati et al., Increased resistance of peptides to serum proteases by modification of their amino groups. Resist peptides against serum proteases. Jan. 8, 2003;58:558-61.

Guimaraes et al., Site-specific C-terminal internal loop labeling of proteins using sortase-mediated reactions. Nat Protoc. 2013;8:1787-99.

Jiang et al., Tumor imaging by means of proteolytic activation of cell-penetrating peptides. Proc. Natl. Acad. Sci. U.S.A. 2004;101:17867-17872.

Liu et al., Structure-based programming of lymph-node targeting in molecular vaccines. Nature. Mar. 27, 2014;507(7493):519-22. doi: 10.1038/nature12978. Epub Feb. 16, 2014.

Nouh et al., Cathepsin B: a potential prognostic marker for inflammatory breast cancer. J Transl Med. 2011;9(1):8 pages.

Olson et al., In vivo characterization of activatable cell penetrating peptides for targeting protease activity in cancer. Integr Biol (Camb). Jun. 2009; 1(5-6):382-93.

Schmid et al., Albumin-binding prodrugs of camptothecin and doxorubicin with an ala-leu-ala-leu-linker that are cleaved by cathepsin b: synthesis and antitumor efficacy. Bioconj Chem. 2007;18(3):702-16.

Trapani et al., Killing by cytotoxic T cells and natural killer cells: multiple granule serine proteases as initiators of DNA fragmentation. Immunol Cell Biol. 1993;71(3):201-8.

Rawlings et al., The MEROPS database of proteolytic enzymes, their substrates and inhibitors in 2017 and a comparison with peptidases in the PANTHER database. Nucleic Acid Res. Jan. 4, 2018;46(D1):D624-D632.

Vandooren et al., Zymography Methods for Visualizing Hydrolytic Enzymes. Nat Methods. Mar. 2013;10(3):211-20. doi: 10.1038/nmeth.2371.

Vasiljeva et al., Monitoring protease activity in biological tissues using antibody prodrugs as sensing probes. Sci Rep. Apr. 3, 2020;10(1):5894.

Wu et al., Expression and clinical significance of matrix metalloproteinase-9 in lymphatic invasiveness and metastasis of breast cancer. PLOS One. 2014;9(5):e97804.

Yan et al., In Situ Zymography: A Molecular Pathology Technique to Localize Endogenous Protease Activity in Tissue Sections. Vet Pathol May 2003;40(3):227-36.

Chen et al., CRISPR-Cas12a target binding unleashes indiscriminate single-stranded DNase activity. Science. Apr. 27, 2018;360(6387):436-439. doi: 10.1126/science.aar6245. Epub Feb. 15, 2018. Erratum in: Science. Feb. 19, 2021;371(6531):PMID: 29449511;PCM6628903.

Gootenberg et al., Multiplexed and portable nucleic acid detection platform with Cas13, Cas12a, and Csm6. Science. Apr. 27, 2018;360(6387):439-444. doi: 10.1126/science.aaq0179. Epub Feb. 15, 2018.

EP 17779900.4, Feb. 12, 2021, Extended European Search Report.

Extended European Search Report for EP Application No. 21172148.5 dated Jan. 10, 2022.

International Preliminary Report on Patentability for International App. No. PCT/US2020/014007 dated Jul. 29, 2021.

International Search Report and Written Opinion for International App. No. PCT/US2020/065547 dated Apr. 15, 2021.

[No Author Listed], Amidase Protein Classification Interpro. 2021. 2 pages.

[No Author Listed], EMBOSS Needle Sequence Alignment. 2021. 2 pages.

Danino et al., Programmable probiotics for detection of cancer in urine. Sci Transl Med. May 27, 2015;7(289):289ra84. doi: 10.1126/scitranslmed.aaa3519. PMID: 26019220; PMCID: PMC4511399.

Farwell et al., PET/CT imaging in cancer: current applications and future directions. Cancer. Nov. 15, 2014;120(22):3433-45. doi: 10.1002/cncr.28860. Epub Jun. 19, 2014. PMID: 24947987.

Gatier et al., Transferrin receptors in human tissues: their distribution and possible clinical relevance. J Clin Pathol. May 1983;36(5):539-45. doi: 10.1136/jcp.36.5.539. PMID: 6302135; PMCID: PMC498283.

Hao et al., CRISPR-Cas-amplified urine biomarkers for multiplexed and portable cancer diagnostics. bioRxiv Jun. 17, 2020.

Jambunathan et al., Prolyl endopeptidase activity in bronchoalveolar lavage fluid: a novel diagnostic biomarker in a guinea pig model of invasive pulmonary aspergillosis. Med Mycol. Aug. 2013;51(6):592-602. doi: 10.3109/13693786.2012.761360. Epub Jan. 28, 2013.

Klan et al., Photoremovable protecting groups in chemistry and biology: reaction mechanisms and efficacy. Chem Rev. Jan. 9, 2013;113(1):119-91. doi: 10.1021/cr300177k. Epub Dec. 21, 2012. PMID: 23256727; PMCID: PMC3557858.

Longo et al., In Vivo Imaging of Tumor Metabolism and Acidosis by Combining PET and MRI-CEST pH Imaging. Cancer Res. Nov. 15, 2016;76(22):6463-6470. doi: 10.1158/0008-5472.CAN-16-0825. Epub Sep. 20, 2016. PMID: 27651313.

Loynachan et al., Renal clearable catalytic gold nanoclusters for in vivo disease monitoring. Nat Nanotechnol. Sep. 2019;14(9):883-890. doi: 10.1038/s41565-019-0527-6. Epub Sep. 2, 2019. PMID: 31477801; PMCID: PMC7045344.

(56) References Cited

OTHER PUBLICATIONS

Parker et al., Folate receptor expression in carcinomas and normal tissues determined by a quantitative radioligand binding assay. Anal Biochem. Mar. 15, 2005;338(2):284-93. doi: 10.1016/j.ab.2004.12. 026. PMID: 15745749.

Rashidian et al., Noninvasive imaging of immune responses. Proc Natl Acad Sci U S A. May 12, 2015;112(19):6146-51. doi: 10.1073/pnas.1502609112. Epub Apr. 20, 2015. Erratum in: Proc Natl Acad Sci U S A. Jul. 3, 2018;115(27):E6387. PMID: 25902531; PMCID: PMC4434737.

Rashidian et al., Predicting the response to CTLA-4 blockade by longitudinal noninvasive monitoring of CD8 T cells. J Exp Med. Aug. 7, 2017;214(8):2243-2255. doi: 10.1084/jem.20161950. Epub Jun. 30, 2017. PMID: 28666979; PMCID: PMC5551571.

Soleimany et al., Activity-Based Diagnostics: An Emerging Paradigm for Disease Detection and Monitoring. Trends Mol Med. May 2020;26(5):450-468. doi: 10.1016/j.molmed.2020.01.013. Epub Apr. 5, 2020. PMID: 32359477; PMCID: PMC8290463.

Sun et al., A PET imaging approach for determining EGFR mutation status for improved lung cancer patient management. Sci Transl Med. Mar. 7, 2018;10(431):eaan8840. doi: 10.1126/scitranslmed. aan8840. PMID: 29515002.

Weerakkody et al., Family of pH (low) insertion peptides for tumor targeting. Proc Natl Acad Sci U S A. Apr. 9, 2013;110(15):5834-9. doi: 10.1073/pnas.1303708110. Epub Mar. 25, 2013. PMID: 23530249; PMCID: PMC3625278.

Yoo et al., 2'-O-methyl-modified phosphorothioate antisense oligonucleotides have reduced non-specific effects in vitro. Nucleic Acids Res. Apr. 2, 2004;32(6):2008-16. doi: 10.1093/nar/gkh516. PMID: 15064360; PMCID: PMC390367.

Zinnhardt et al., Combined PET Imaging of the Inflammatory Tumor Microenvironment Identifies Margins of Unique Radiotracer Uptake. Cancer Res. Apr. 15, 2017;77(8):1831-1841. doi: 10.1158/0008-5472.CAN-16-2628. Epub Jan. 30, 2017. PMID: 28137769.

\* cited by examiner

```
                         SEQUENCE LISTING

<160> NUMBER OF SEQ ID NOS: 81

<210> SEQ ID NO 1
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 1

Glu Gly Val Asn Asp Asn Glu Glu Gly Phe Phe Ser Ala Arg
1               5                   10

<210> SEQ ID NO 2
<211> LENGTH: 11
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (1)..(1)
<223> OTHER INFORMATION: Modified with 5FAM
<220> FEATURE:
<221> NAME/KEY: misc_feature
<222> LOCATION: (10)..(11)
<223> OTHER INFORMATION: Modified with CPQ2-PEG2

<400> SEQUENCE: 2

Gly Gly Pro Gln Gly Ile Trp Gly Gln Lys Cys
1               5                   10

<210> SEQ ID NO 3
<211> LENGTH: 11
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (1)..(1)
<223> OTHER INFORMATION: Modified with 5FAM
<220> FEATURE:
<221> NAME/KEY: misc_feature
<222> LOCATION: (10)..(11)
<223> OTHER INFORMATION: Modified with CPQ2-PEG2

<400> SEQUENCE: 3

Gly Gly Leu Val Pro Arg Gly Ser Gly Lys Cys
1               5                   10

<210> SEQ ID NO 4
<211> LENGTH: 10
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (1)..(1)
<223> OTHER INFORMATION: Modified with 5FAM
<220> FEATURE:
<221> NAME/KEY: misc_feature
<222> LOCATION: (9)..(10)
<223> OTHER INFORMATION: Modified with CPQ2-PEG2
```

```
<400> SEQUENCE: 4

Gly Gly Pro Val Gly Leu Ile Gly Lys Cys
1               5                   10

<210> SEQ ID NO 5
<211> LENGTH: 12
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (1)..(1)
<223> OTHER INFORMATION: Modified with 5FAM
<220> FEATURE:
<221> NAME/KEY: misc_feature
<222> LOCATION: (11)..(12)
<223> OTHER INFORMATION: Modified with CPQ2-PEG2

<400> SEQUENCE: 5

Gly Gly Pro Trp Gly Ile Trp Gly Gln Gly Lys Cys
1               5                   10

<210> SEQ ID NO 6
<211> LENGTH: 12
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (1)..(1)
<223> OTHER INFORMATION: Modified with 5FAM
<220> FEATURE:
<221> NAME/KEY: misc_feature
<222> LOCATION: (11)..(12)
<223> OTHER INFORMATION: Modified with CPQ2-PEG2

<400> SEQUENCE: 6

Gly Gly Pro Val Pro Leu Ser Leu Val Met Lys Cys
1               5                   10

<210> SEQ ID NO 7
<211> LENGTH: 11
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (1)..(1)
<223> OTHER INFORMATION: Modified with 5FAM
<220> FEATURE:
<221> NAME/KEY: misc_feature
<222> LOCATION: (10)..(11)
<223> OTHER INFORMATION: Modified with CPQ2-PEG2

<400> SEQUENCE: 7

Gly Gly Pro Leu Gly Leu Arg Ser Trp Lys Cys
1               5                   10

<210> SEQ ID NO 8
<211> LENGTH: 11
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (1)..(1)
<223> OTHER INFORMATION: Modified with 5FAM
```

```
<220> FEATURE:
<221> NAME/KEY: misc_feature
<222> LOCATION: (10)..(11)
<223> OTHER INFORMATION: Modified with CPQ2-PEG2

<400> SEQUENCE: 8

Gly Gly Pro Leu Gly Val Arg Gly Lys Lys Cys
1               5                   10

<210> SEQ ID NO 9
<211> LENGTH: 10
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (1)..(1)
<223> OTHER INFORMATION: Modified with 5FAM
<220> FEATURE:
<221> NAME/KEY: mod_res
<222> LOCATION: (3)..(3)
<223> OTHER INFORMATION: D stereoisomer of Phe
<220> FEATURE:
<221> NAME/KEY: misc_feature
<222> LOCATION: (3)..(4)
<223> OTHER INFORMATION: Modified with pipecolic acid
<220> FEATURE:
<221> NAME/KEY: misc_feature
<222> LOCATION: (9)..(10)
<223> OTHER INFORMATION: Modified with CPQ2-PEG2

<400> SEQUENCE: 9

Gly Gly Phe Arg Ser Gly Gly Gly Lys Cys
1               5                   10

<210> SEQ ID NO 10
<211> LENGTH: 11
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (1)..(1)
<223> OTHER INFORMATION: Modified with 5FAM
<220> FEATURE:
<221> NAME/KEY: mod_res
<222> LOCATION: (3)..(3)
<223> OTHER INFORMATION: D stereoisomer of Phe
<220> FEATURE:
<221> NAME/KEY: misc_feature
<222> LOCATION: (10)..(11)
<223> OTHER INFORMATION: Modified with CPQ2-PEG2

<400> SEQUENCE: 10

Gly Gly Phe Pro Arg Ser Gly Gly Gly Lys Cys
1               5                   10

<210> SEQ ID NO 11
<211> LENGTH: 10
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (1)..(1)
<223> OTHER INFORMATION: Modified with 5FAM
<220> FEATURE:
<221> NAME/KEY: mod_res
<222> LOCATION: (3)..(3)
<223> OTHER INFORMATION: D stereoisomer of Phe
```

```
<220> FEATURE:
<221> NAME/KEY: misc_feature
<222> LOCATION: (3)..(4)
<223> OTHER INFORMATION: Modified with pipecolic acid
<220> FEATURE:
<221> NAME/KEY: misc_feature
<222> LOCATION: (9)..(10)
<223> OTHER INFORMATION: Modified with CPQ2-PEG2

<400> SEQUENCE: 11

Gly Gly Phe Lys Ser Gly Gly Gly Lys Cys
1               5                   10

<210> SEQ ID NO 12
<211> LENGTH: 12
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (1)..(1)
<223> OTHER INFORMATION: Modified with 5FAM
<220> FEATURE:
<221> NAME/KEY: misc_feature
<222> LOCATION: (11)..(12)
<223> OTHER INFORMATION: Modified with CPQ2-PEG2

<400> SEQUENCE: 12

Gly Gly Ala Ala Glu Ala Ile Ser Asp Ala Lys Cys
1               5                   10

<210> SEQ ID NO 13
<211> LENGTH: 12
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (1)..(1)
<223> OTHER INFORMATION: Modified with 5FAM
<220> FEATURE:
<221> NAME/KEY: misc_feature
<222> LOCATION: (11)..(12)
<223> OTHER INFORMATION: Modified with CPQ2-PEG2

<400> SEQUENCE: 13

Gly Gly Ala Gly Gly Ala Gln Met Gly Ala Lys Cys
1               5                   10

<210> SEQ ID NO 14
<211> LENGTH: 12
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (1)..(1)
<223> OTHER INFORMATION: Modified with 5FAM
<220> FEATURE:
<221> NAME/KEY: misc_feature
<222> LOCATION: (11)..(12)
<223> OTHER INFORMATION: Modified with CPQ2-PEG2

<400> SEQUENCE: 14

Gly Gly Ala Gln Pro Asp Ala Leu Asn Val Lys Cys
1               5                   10
```

```
<210> SEQ ID NO 15
<211> LENGTH: 12
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (1)..(1)
<223> OTHER INFORMATION: Modified with 5FAM
<220> FEATURE:
<221> NAME/KEY: misc_feature
<222> LOCATION: (11)..(12)
<223> OTHER INFORMATION: Modified with CPQ2-PEG2

<400> SEQUENCE: 15

Gly Gly Ala Thr Asp Val Thr Thr Thr Pro Lys Cys
1               5                   10

<210> SEQ ID NO 16
<211> LENGTH: 12
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (1)..(1)
<223> OTHER INFORMATION: Modified with 5FAM
<220> FEATURE:
<221> NAME/KEY: misc_feature
<222> LOCATION: (11)..(12)
<223> OTHER INFORMATION: Modified with CPQ2-PEG2

<400> SEQUENCE: 16

Gly Gly Asp Ile Val Thr Val Ala Asn Ala Lys Cys
1               5                   10

<210> SEQ ID NO 17
<211> LENGTH: 12
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (1)..(1)
<223> OTHER INFORMATION: Modified with 5FAM
<220> FEATURE:
<221> NAME/KEY: misc_feature
<222> LOCATION: (11)..(12)
<223> OTHER INFORMATION: Modified with CPQ2-PEG2

<400> SEQUENCE: 17

Gly Gly Asp Leu Gly Leu Lys Ser Val Pro Lys Cys
1               5                   10

<210> SEQ ID NO 18
<211> LENGTH: 12
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (1)..(1)
<223> OTHER INFORMATION: Modified with 5FAM
<220> FEATURE:
<221> NAME/KEY: misc_feature
<222> LOCATION: (11)..(12)
<223> OTHER INFORMATION: Modified with CPQ2-PEG2
```

-continued

```
<400> SEQUENCE: 18

Gly Gly Asp Val Met Ala Ser Gln Lys Arg Lys Cys
1               5                   10

<210> SEQ ID NO 19
<211> LENGTH: 12
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (1)..(1)
<223> OTHER INFORMATION: Modified with 5FAM
<220> FEATURE:
<221> NAME/KEY: misc_feature
<222> LOCATION: (11)..(12)
<223> OTHER INFORMATION: Modified with CPQ2-PEG2

<400> SEQUENCE: 19

Gly Gly Glu Ser Asp Glu Leu Gln Thr Ile Lys Cys
1               5                   10

<210> SEQ ID NO 20
<211> LENGTH: 12
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (1)..(1)
<223> OTHER INFORMATION: Modified with 5FAM
<220> FEATURE:
<221> NAME/KEY: misc_feature
<222> LOCATION: (11)..(12)
<223> OTHER INFORMATION: Modified with CPQ2-PEG2

<400> SEQUENCE: 20

Gly Gly Phe His Pro Leu His Ser Lys Ile Lys Cys
1               5                   10

<210> SEQ ID NO 21
<211> LENGTH: 12
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (1)..(1)
<223> OTHER INFORMATION: Modified with 5FAM
<220> FEATURE:
<221> NAME/KEY: misc_feature
<222> LOCATION: (11)..(12)
<223> OTHER INFORMATION: Modified with CPQ2-PEG2

<400> SEQUENCE: 21

Gly Gly Gly His Ala Arg Leu Val His Val Lys Cys
1               5                   10

<210> SEQ ID NO 22
<211> LENGTH: 12
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (1)..(1)
<223> OTHER INFORMATION: Modified with 5FAM
```

```
<220> FEATURE:
<221> NAME/KEY: misc_feature
<222> LOCATION: (11)..(12)
<223> OTHER INFORMATION: Modified with CPQ2-PEG2

<400> SEQUENCE: 22

Gly Gly His Ile Ala Asn Val Glu Arg Val Lys Cys
1               5                   10

<210> SEQ ID NO 23
<211> LENGTH: 12
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (1)..(1)
<223> OTHER INFORMATION: Modified with 5FAM
<220> FEATURE:
<221> NAME/KEY: misc_feature
<222> LOCATION: (11)..(12)
<223> OTHER INFORMATION: Modified with CPQ2-PEG2

<400> SEQUENCE: 23

Gly Gly Lys Ala Ala Ala Thr Gln Lys Lys Lys Cys
1               5                   10

<210> SEQ ID NO 24
<211> LENGTH: 12
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (1)..(1)
<223> OTHER INFORMATION: Modified with 5FAM
<220> FEATURE:
<221> NAME/KEY: misc_feature
<222> LOCATION: (11)..(12)
<223> OTHER INFORMATION: Modified with CPQ2-PEG2

<400> SEQUENCE: 24

Gly Gly Leu Ala Thr Ala Ser Thr Met Asp Lys Cys
1               5                   10

<210> SEQ ID NO 25
<211> LENGTH: 12
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (1)..(1)
<223> OTHER INFORMATION: Modified with 5FAM
<220> FEATURE:
<221> NAME/KEY: misc_feature
<222> LOCATION: (11)..(12)
<223> OTHER INFORMATION: Modified with CPQ2-PEG2

<400> SEQUENCE: 25

Gly Gly Leu Gly Pro Lys Gly Gln Thr Gly Lys Cys
1               5                   10

<210> SEQ ID NO 26
<211> LENGTH: 12
<212> TYPE: PRT
<213> ORGANISM: Artificial Sequence
```

```
<220> FEATURE:
<223> OTHER INFORMATION: Synthetic Polypeptide
<220> FEATURE:
<221> NAME/KEY: misc_feature
<222> LOCATION: (1)..(1)
<223> OTHER INFORMATION: Modified with 5FAM
<220> FEATURE:
<221> NAME/KEY: misc_feature
<222> LOCATION: (11)..(12)
<223> OTHER INFORMATION: Modified with CPQ2-PEG2

<400> SEQUENCE: 26

Gly Gly Leu Ser Leu Pro Glu Thr Gly Glu Lys Cys
1               5                   10

<210> SEQ ID NO 27
<211> LENGTH: 12
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (1)..(1)
<223> OTHER INFORMATION: Modified with 5FAM
<220> FEATURE:
<221> NAME/KEY: misc_feature
<222> LOCATION: (11)..(12)
<223> OTHER INFORMATION: Modified with CPQ2-PEG2

<400> SEQUENCE: 27

Gly Gly Asn Leu Ala Gly Ile Leu Lys Glu Lys Cys
1               5                   10

<210> SEQ ID NO 28
<211> LENGTH: 12
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (1)..(1)
<223> OTHER INFORMATION: Modified with 5FAM
<220> FEATURE:
<221> NAME/KEY: misc_feature
<222> LOCATION: (11)..(12)
<223> OTHER INFORMATION: Modified with CPQ2-PEG2

<400> SEQUENCE: 28

Gly Gly Asn Pro Gly Met Ser Glu Pro Val Lys Cys
1               5                   10

<210> SEQ ID NO 29
<211> LENGTH: 11
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (1)..(1)
<223> OTHER INFORMATION: Modified with 5FAM
<220> FEATURE:
<221> NAME/KEY: misc_feature
<222> LOCATION: (11)..(12)
<223> OTHER INFORMATION: Modified with CPQ2-PEG2

<400> SEQUENCE: 29

Gly Gly Pro Phe Gly Cys His Ala Lys Lys Cys
1               5                   10
```

<210> SEQ ID NO 30
<211> LENGTH: 11
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (1)..(1)
<223> OTHER INFORMATION: Modified with 5FAM
<220> FEATURE:
<221> NAME/KEY: misc_feature
<222> LOCATION: (10)..(11)
<223> OTHER INFORMATION: Modified with CPQ2-PEG2

<400> SEQUENCE: 30

Gly Gly Pro Leu Gly Leu Arg Trp Trp Lys Cys
1               5                   10

<210> SEQ ID NO 31
<211> LENGTH: 12
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (1)..(1)
<223> OTHER INFORMATION: Modified with 5FAM
<220> FEATURE:
<221> NAME/KEY: misc_feature
<222> LOCATION: (11)..(12)
<223> OTHER INFORMATION: Modified with CPQ2-PEG2

<400> SEQUENCE: 31

Gly Gly Gln Met Gly Val Met Gln Gly Val Lys Cys
1               5                   10

<210> SEQ ID NO 32
<211> LENGTH: 12
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (1)..(1)
<223> OTHER INFORMATION: Modified with 5FAM
<220> FEATURE:
<221> NAME/KEY: misc_feature
<222> LOCATION: (11)..(12)
<223> OTHER INFORMATION: Modified with CPQ2-PEG2

<400> SEQUENCE: 32

Gly Gly Gln Thr Cys Lys Cys Ser Cys Lys Lys Cys
1               5                   10

<210> SEQ ID NO 33
<211> LENGTH: 12
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (1)..(1)
<223> OTHER INFORMATION: Modified with 5FAM
<220> FEATURE:
<221> NAME/KEY: misc_feature
<222> LOCATION: (11)..(12)
<223> OTHER INFORMATION: Modified with CPQ2-PEG2

-continued

```
<400> SEQUENCE: 33

Gly Gly Gln Trp Ala Gly Leu Val Glu Lys Lys Cys
1               5                   10

<210> SEQ ID NO 34
<211> LENGTH: 12
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (1)..(1)
<223> OTHER INFORMATION: Modified with 5FAM
<220> FEATURE:
<221> NAME/KEY: misc_feature
<222> LOCATION: (11)..(12)
<223> OTHER INFORMATION: Modified with CPQ2-PEG2

<400> SEQUENCE: 34

Gly Gly Arg Pro Ala Val Met Thr Ser Pro Lys Cys
1               5                   10

<210> SEQ ID NO 35
<211> LENGTH: 12
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (1)..(1)
<223> OTHER INFORMATION: Modified with 5FAM
<220> FEATURE:
<221> NAME/KEY: misc_feature
<222> LOCATION: (11)..(12)
<223> OTHER INFORMATION: Modified with CPQ2-PEG2

<400> SEQUENCE: 35

Gly Gly Thr Leu Arg Glu Leu His Leu Asp Lys Cys
1               5                   10

<210> SEQ ID NO 36
<211> LENGTH: 12
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (1)..(1)
<223> OTHER INFORMATION: Modified with 5FAM
<220> FEATURE:
<221> NAME/KEY: misc_feature
<222> LOCATION: (11)..(12)
<223> OTHER INFORMATION: Modified with CPQ2-PEG2

<400> SEQUENCE: 36

Gly Gly Thr Pro Pro Ser Gln Gly Lys Lys Cys
1               5                   10

<210> SEQ ID NO 37
<211> LENGTH: 12
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (1)..(1)
<223> OTHER INFORMATION: Modified with 5FAM
```

```
<220> FEATURE:
<221> NAME/KEY: misc_feature
<222> LOCATION: (11)..(12)
<223> OTHER INFORMATION: Modified with CPQ2-PEG2

<400> SEQUENCE: 37

Gly Gly Thr Ser Glu Asp Leu Val Val Gln Lys Cys
1               5                   10

<210> SEQ ID NO 38
<211> LENGTH: 12
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (1)..(1)
<223> OTHER INFORMATION: Modified with 5FAM
<220> FEATURE:
<221> NAME/KEY: misc_feature
<222> LOCATION: (11)..(12)
<223> OTHER INFORMATION: Modified with CPQ2-PEG2

<400> SEQUENCE: 38

Gly Gly Val Trp Ala Ala Glu Ala Ile Ser Lys Cys
1               5                   10

<210> SEQ ID NO 39
<211> LENGTH: 13
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (1)..(1)
<223> OTHER INFORMATION: Modified with 5FAM
<220> FEATURE:
<221> NAME/KEY: misc_feature
<222> LOCATION: (11)..(12)
<223> OTHER INFORMATION: Modified with CPQ2-PEG2

<400> SEQUENCE: 39

Gly Arg Gln Arg Arg Ala Leu Glu Lys Gly Lys Gly Cys
1               5                   10

<210> SEQ ID NO 40
<211> LENGTH: 15
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (1)..(1)
<223> OTHER INFORMATION: Modified with 5FAM
<220> FEATURE:
<221> NAME/KEY: misc_feature
<222> LOCATION: (13)..(14)
<223> OTHER INFORMATION: Modified with CPQ2-PEG2

<400> SEQUENCE: 40

Gly Gly Gly Ser Gly Arg Ser Ala Asn Ala Lys Gly Lys Gly Cys
1               5                   10                  15

<210> SEQ ID NO 41
<211> LENGTH: 13
<212> TYPE: PRT
<213> ORGANISM: Artificial Sequence
```

```
<220> FEATURE:
<223> OTHER INFORMATION: Synthetic Polypeptide
<220> FEATURE:
<221> NAME/KEY: misc_feature
<222> LOCATION: (1)..(1)
<223> OTHER INFORMATION: Modified with 5FAM
<220> FEATURE:
<221> NAME/KEY: misc_feature
<222> LOCATION: (11)..(12)
<223> OTHER INFORMATION: Modified with CPQ2-PEG2

<400> SEQUENCE: 41

Gly Lys Pro Ile Ser Leu Ile Ser Ser Gly Lys Gly Cys
1               5                   10

<210> SEQ ID NO 42
<211> LENGTH: 13
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (1)..(1)
<223> OTHER INFORMATION: Modified with 5FAM
<220> FEATURE:
<221> NAME/KEY: misc_feature
<222> LOCATION: (11)..(12)
<223> OTHER INFORMATION: Modified with CPQ2-PEG2

<400> SEQUENCE: 42

Gly Ile Leu Ser Arg Ile Val Gly Gly Gly Lys Gly Cys
1               5                   10

<210> SEQ ID NO 43
<211> LENGTH: 8
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (1)..(1)
<223> OTHER INFORMATION: Modified with 5FAM
<220> FEATURE:
<221> NAME/KEY: misc_feature
<222> LOCATION: (6)..(7)
<223> OTHER INFORMATION: Modified with CPQ2-PEG2

<400> SEQUENCE: 43

Gly Gly Gly Pro Gly Lys Gly Cys
1               5

<210> SEQ ID NO 44
<211> LENGTH: 14
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (1)..(1)
<223> OTHER INFORMATION: Modified with 5FAM
<220> FEATURE:
<221> NAME/KEY: misc_feature
<222> LOCATION: (7)..(8)
<223> OTHER INFORMATION: Modified with Nval
<220> FEATURE:
<221> NAME/KEY: misc_feature
<222> LOCATION: (12)..(13)
<223> OTHER INFORMATION: Modified with CPQ2-PEG2
```

```
<400> SEQUENCE: 44

Gly Arg Pro Lys Pro Val Glu Trp Arg Lys Gly Lys Gly Cys
1               5                   10

<210> SEQ ID NO 45
<211> LENGTH: 11
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (1)..(1)
<223> OTHER INFORMATION: Modified with 5FAM
<220> FEATURE:
<221> NAME/KEY: misc_feature
<222> LOCATION: (9)..(10)
<223> OTHER INFORMATION: Modified with CPQ2-PEG2

<400> SEQUENCE: 45

Gly His Ser Ser Lys Leu Gln Gly Lys Gly Cys
1               5                   10

<210> SEQ ID NO 46
<211> LENGTH: 13
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (1)..(1)
<223> OTHER INFORMATION: Modified with 5FAM
<220> FEATURE:
<221> NAME/KEY: misc_feature
<222> LOCATION: (11)..(12)
<223> OTHER INFORMATION: Modified with CPQ2-PEG2

<400> SEQUENCE: 46

Gly Ser Ser Gln Tyr Ser Ser Asn Gly Gly Lys Gly Cys
1               5                   10

<210> SEQ ID NO 47
<211> LENGTH: 13
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (1)..(1)
<223> OTHER INFORMATION: Modified with 5FAM
<220> FEATURE:
<221> NAME/KEY: misc_feature
<222> LOCATION: (11)..(12)
<223> OTHER INFORMATION: Modified with CPQ2-PEG2

<400> SEQUENCE: 47

Gly Gln Lys Gly Arg Tyr Lys Gln Glu Gly Lys Gly Cys
1               5                   10

<210> SEQ ID NO 48
<211> LENGTH: 13
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (1)..(1)
<223> OTHER INFORMATION: Modified with 5FAM
```

```
<220> FEATURE:
<221> NAME/KEY: misc_feature
<222> LOCATION: (11)..(12)
<223> OTHER INFORMATION: Modified with CPQ2-PEG2

<400> SEQUENCE: 48

Gly Gly Lys Ala Phe Arg Arg Ser Gly Gly Lys Gly Cys
1               5                   10

<210> SEQ ID NO 49
<211> LENGTH: 13
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (1)..(1)
<223> OTHER INFORMATION: Modified with 5FAM
<220> FEATURE:
<221> NAME/KEY: misc_feature
<222> LOCATION: (11)..(12)
<223> OTHER INFORMATION: Modified with CPQ2-PEG2

<400> SEQUENCE: 49

Gly Ile Gln Gln Arg Ser Leu Gly Gly Gly Lys Gly Cys
1               5                   10

<210> SEQ ID NO 50
<211> LENGTH: 10
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (1)..(1)
<223> OTHER INFORMATION: Modified with 5FAM
<220> FEATURE:
<221> NAME/KEY: misc_feature
<222> LOCATION: (8)..(9)
<223> OTHER INFORMATION: Modified with CPQ2-PEG2

<400> SEQUENCE: 50

Gly Gly Val Pro Arg Gly Gly Lys Gly Cys
1               5                   10

<210> SEQ ID NO 51
<211> LENGTH: 13
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (1)..(1)
<223> OTHER INFORMATION: Modified with 5FAM
<220> FEATURE:
<221> NAME/KEY: misc_feature
<222> LOCATION: (11)..(12)
<223> OTHER INFORMATION: Modified with CPQ2-PEG2

<400> SEQUENCE: 51

Gly Ser Gly Ser Lys Ile Ile Gly Gly Gly Lys Gly Cys
1               5                   10

<210> SEQ ID NO 52
<211> LENGTH: 11
<212> TYPE: PRT
<213> ORGANISM: Artificial Sequence
```

```
<220> FEATURE:
<223> OTHER INFORMATION: Synthetic Polypeptide
<220> FEATURE:
<221> NAME/KEY: misc_feature
<222> LOCATION: (1)..(1)
<223> OTHER INFORMATION: Modified with 5FAM
<220> FEATURE:
<221> NAME/KEY: misc_feature
<222> LOCATION: (9)..(10)
<223> OTHER INFORMATION: Modified with CPQ2-PEG2

<400> SEQUENCE: 52

Gly Ala Ala Asn Leu Thr Arg Gly Lys Gly Cys
1               5                   10

<210> SEQ ID NO 53
<211> LENGTH: 10
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (1)..(1)
<223> OTHER INFORMATION: Modified with 5FAM
<220> FEATURE:
<221> NAME/KEY: misc_feature
<222> LOCATION: (8)..(9)
<223> OTHER INFORMATION: Modified with CPQ2-PEG2

<400> SEQUENCE: 53

Gly Gly Gly Glu Leu Arg Gly Lys Gly Cys
1               5                   10

<210> SEQ ID NO 54
<211> LENGTH: 11
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (1)..(1)
<223> OTHER INFORMATION: Modified with 5FAM
<220> FEATURE:
<221> NAME/KEY: misc_feature
<222> LOCATION: (5)..(6)
<223> OTHER INFORMATION: Modified with Phe(homo)
<220> FEATURE:
<221> NAME/KEY: misc_feature
<222> LOCATION: (9)..(10)
<223> OTHER INFORMATION: Modified with CPQ2-PEG2

<400> SEQUENCE: 54

Gly Leu Ala Gln Ala Arg Ser Gly Lys Gly Cys
1               5                   10

<210> SEQ ID NO 55
<211> LENGTH: 15
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (1)..(1)
<223> OTHER INFORMATION: Modified with 5FAM
<220> FEATURE:
<221> NAME/KEY: misc_feature
<222> LOCATION: (13)..(14)
<223> OTHER INFORMATION: Modified with CPQ2-PEG2
```

-continued

<400> SEQUENCE: 55

Gly Ser Pro Leu Ala Gln Ala Val Arg Ser Ser Gly Lys Gly Cys
1               5                   10                  15

<210> SEQ ID NO 56
<211> LENGTH: 10
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (1)..(1)
<223> OTHER INFORMATION: Modified with 5FAM
<220> FEATURE:
<221> NAME/KEY: misc_feature
<222> LOCATION: (8)..(9)
<223> OTHER INFORMATION: Modified with CPQ2-PEG2

<400> SEQUENCE: 56

Gly Met Glu Arg Met Gly Gly Lys Gly Cys
1               5                   10

<210> SEQ ID NO 57
<211> LENGTH: 13
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (1)..(1)
<223> OTHER INFORMATION: Modified with 5FAM
<220> FEATURE:
<221> NAME/KEY: misc_feature
<222> LOCATION: (11)..(12)
<223> OTHER INFORMATION: Modified with CPQ2-PEG2

<400> SEQUENCE: 57

Gly Pro Val Pro Leu Ser Leu Val Met Gly Lys Gly Cys
1               5                   10

<210> SEQ ID NO 58
<211> LENGTH: 13
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (1)..(1)
<223> OTHER INFORMATION: Modified with 5FAM
<220> FEATURE:
<221> NAME/KEY: misc_feature
<222> LOCATION: (11)..(12)
<223> OTHER INFORMATION: Modified with CPQ2-PEG2

<400> SEQUENCE: 58

Gly Arg Gln Ser Arg Ile Val Gly Gly Gly Lys Gly Cys
1               5                   10

<210> SEQ ID NO 59
<211> LENGTH: 13
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (1)..(1)
<223> OTHER INFORMATION: Modified with 5FAM

```
<220> FEATURE:
<221> NAME/KEY: misc_feature
<222> LOCATION: (11)..(12)
<223> OTHER INFORMATION: Modified with CPQ2-PEG2

<400> SEQUENCE: 59

Gly Ser Gln Pro Arg Ile Val Gly Gly Gly Lys Gly Cys
1               5                   10

<210> SEQ ID NO 60
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 60

Asp Ile Cys Leu Pro Arg Trp Gly Cys Leu Trp
1               5                   10

<210> SEQ ID NO 61
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 61

Ser Leu Lys Arg Tyr Gly Gly Gly
1               5

<210> SEQ ID NO 62
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 62

Ala Ala Phe Arg Ser Arg Gly Ala
1               5

<210> SEQ ID NO 63
<211> LENGTH: 8
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (7)..(8)
<223> OTHER INFORMATION: Xaa can be any naturally occurring amino acid

<400> SEQUENCE: 63

Xaa Xaa Phe Arg Phe Phe Xaa Xaa
1               5

<210> SEQ ID NO 64
<211> LENGTH: 6
<212> TYPE: PRT
<213> ORGANISM: Artificial Sequence
<220> FEATURE:
<223> OTHER INFORMATION: Synthetic Polypeptide
```

```
<400> SEQUENCE: 64

Gln Ser Val Gly Phe Ala
1               5

<210> SEQ ID NO 65
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 65

Leu Gly Leu Glu Gly Ala Asp
1               5

<210> SEQ ID NO 66
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 66

Gly Pro Leu Asp
1

<210> SEQ ID NO 67
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 67

Leu Gly Val Leu Ile Val
1               5

<210> SEQ ID NO 68
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 68

Gly Leu Val Leu Val Ala
1               5

<210> SEQ ID NO 69
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 69

Pro Ala Ala Leu Val Gly
1               5

<210> SEQ ID NO 70
<211> LENGTH: 7
<212> TYPE: PRT
<213> ORGANISM: Artificial Sequence
<220> FEATURE:
<223> OTHER INFORMATION: Synthetic Polypeptide
```

```
<400> SEQUENCE: 70

Gly Pro Ala Gly Leu Ala Gly
1               5

<210> SEQ ID NO 71
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 71

Ala Ser Pro Arg Ala Gly Gly Lys
1               5

<210> SEQ ID NO 72
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 72

Tyr Glu Ala Asp Ser Leu Glu Glu
1               5

<210> SEQ ID NO 73
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 73

Tyr Gln Tyr Arg Ala Leu
1               5

<210> SEQ ID NO 74
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 74

Gly Gly Val Pro Arg Gly
1               5

<210> SEQ ID NO 75
<211> LENGTH: 25
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (1)..(1)
<223> OTHER INFORMATION: Modified with Albumin
<220> FEATURE:
<221> NAME/KEY: misc_feature
<222> LOCATION: (10)..(11)
<223> OTHER INFORMATION: Modified with Biotin
<220> FEATURE:
<221> NAME/KEY: mod_res
<222> LOCATION: (11)..(11)
<223> OTHER INFORMATION: D stereoisomer of Glu
```

```
<220> FEATURE:
<221> NAME/KEY: mod_res
<222> LOCATION: (13)..(13)
<223> OTHER INFORMATION: D stereoisomer of Val
<220> FEATURE:
<221> NAME/KEY: mod_res
<222> LOCATION: (14)..(14)
<223> OTHER INFORMATION: D stereoisomer of Asn
<220> FEATURE:
<221> NAME/KEY: mod_res
<222> LOCATION: (15)..(15)
<223> OTHER INFORMATION: D stereoisomer of Asp
<220> FEATURE:
<221> NAME/KEY: mod_res
<222> LOCATION: (16)..(16)
<223> OTHER INFORMATION: D stereoisomer of Asn
<220> FEATURE:
<221> NAME/KEY: mod_res
<222> LOCATION: (17)..(17)
<223> OTHER INFORMATION: D stereoisomer of Glu
<220> FEATURE:
<221> NAME/KEY: mod_res
<222> LOCATION: (18)..(18)
<223> OTHER INFORMATION: D stereoisomer of Glu
<220> FEATURE:
<221> NAME/KEY: mod_res
<222> LOCATION: (20)..(20)
<223> OTHER INFORMATION: D stereoisomer of Phe
<220> FEATURE:
<221> NAME/KEY: mod_res
<222> LOCATION: (21)..(21)
<223> OTHER INFORMATION: D stereoisomer of Phe
<220> FEATURE:
<221> NAME/KEY: mod_res
<222> LOCATION: (22)..(22)
<223> OTHER INFORMATION: D stereoisomer of Ser
<220> FEATURE:
<221> NAME/KEY: mod_res
<222> LOCATION: (23)..(23)
<223> OTHER INFORMATION: D stereoisomer of Ala
<220> FEATURE:
<221> NAME/KEY: mod_res
<222> LOCATION: (24)..(24)
<223> OTHER INFORMATION: D stereoisomer of Arg
<220> FEATURE:
<221> NAME/KEY: misc_feature
<222> LOCATION: (25)..(25)
<223> OTHER INFORMATION: Modified with FAM

<400> SEQUENCE: 75

Gly Pro Leu Gly Val Arg Gly Lys Gly Lys Glu Gly Val Asn Asp Asn
1               5                   10                  15

Glu Glu Gly Phe Phe Ser Ala Arg Lys
            20                  25

<210> SEQ ID NO 76
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 76

Pro Leu Gly Val Arg Gly Lys
1               5

<210> SEQ ID NO 77
<211> LENGTH: 16
<212> TYPE: PRT
<213> ORGANISM: Artificial Sequence
<220> FEATURE:
<223> OTHER INFORMATION: Synthetic Polypeptide
```

```
<220> FEATURE:
<221> NAME/KEY: misc_feature
<222> LOCATION: (1)..(2)
<223> OTHER INFORMATION: Modified with Biotin
<220> FEATURE:
<221> NAME/KEY: mod_res
<222> LOCATION: (2)..(2)
<223> OTHER INFORMATION: D stereoisomer of Glu
<220> FEATURE:
<221> NAME/KEY: mod_res
<222> LOCATION: (4)..(4)
<223> OTHER INFORMATION: D stereoisomer of Val
<220> FEATURE:
<221> NAME/KEY: mod_res
<222> LOCATION: (5)..(5)
<223> OTHER INFORMATION: D stereoisomer of Asn
<220> FEATURE:
<221> NAME/KEY: mod_res
<222> LOCATION: (6)..(6)
<223> OTHER INFORMATION: D stereoisomer of Asp
<220> FEATURE:
<221> NAME/KEY: mod_res
<222> LOCATION: (7)..(7)
<223> OTHER INFORMATION: D stereoisomer of Asn
<220> FEATURE:
<221> NAME/KEY: mod_res
<222> LOCATION: (8)..(8)
<223> OTHER INFORMATION: D stereoisomer of Glu
<220> FEATURE:
<221> NAME/KEY: mod_res
<222> LOCATION: (9)..(9)
<223> OTHER INFORMATION: D stereoisomer of Glu
<220> FEATURE:
<221> NAME/KEY: mod_res
<222> LOCATION: (11)..(11)
<223> OTHER INFORMATION: D stereoisomer of Phe
<220> FEATURE:
<221> NAME/KEY: mod_res
<222> LOCATION: (12)..(12)
<223> OTHER INFORMATION: D stereoisomer of Phe
<220> FEATURE:
<221> NAME/KEY: mod_res
<222> LOCATION: (13)..(13)
<223> OTHER INFORMATION: D stereoisomer of Ser
<220> FEATURE:
<221> NAME/KEY: mod_res
<222> LOCATION: (14)..(14)
<223> OTHER INFORMATION: D stereoisomer of Ala
<220> FEATURE:
<221> NAME/KEY: mod_res
<222> LOCATION: (15)..(15)
<223> OTHER INFORMATION: D stereoisomer of Arg
<220> FEATURE:
<221> NAME/KEY: misc_feature
<222> LOCATION: (16)..(16)
<223> OTHER INFORMATION: Modified with FAM

<400> SEQUENCE: 77

Lys Glu Gly Val Asn Asp Asn Glu Glu Gly Phe Phe Ser Ala Arg Lys
1               5                   10                  15

<210> SEQ ID NO 78
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 78

Cys Ala Val Gly Ala Leu Glu Gly Pro Arg Asn Gln Asp Trp Leu Gly
1               5                   10                  15

Val Pro Arg Gln Leu
            20
```

```
<210> SEQ ID NO 79
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 79
tccatgacgt tcctgacgtt                                                    20

<210> SEQ ID NO 80
<211> LENGTH: 6
<212> TYPE: PRT
<213> ORGANISM: Artificial Sequence
<220> FEATURE:
<223> OTHER INFORMATION: Synthetic Polypeptide
<220> FEATURE:
<221> NAME/KEY: mod_res
<222> LOCATION: (1)..(1)
<223> OTHER INFORMATION: D stereoisomer of Phe
<220> FEATURE:
<221> NAME/KEY: misc_feature
<222> LOCATION: (1)..(2)
<223> OTHER INFORMATION: Modified with pipecolic acid

<400> SEQUENCE: 80

Phe Lys Ser Gly Gly Gly
1               5

<210> SEQ ID NO 81
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 81

Leu Pro Ser Thr Gly His His His His His His
1               5                   10
```

METHODS TO SPECIFICALLY PROFILE PROTEASE ACTIVITY AT LYMPH NODES

RELATED APPLICATIONS

This application is a national stage filing under 35 U.S.C. § 371 of International Application No. PCT/US2017/026564, filed Apr. 7, 2017, which claims the benefit under 35 U.S.C. § 119(e) of U.S. provisional Application Ser. No. 62/319,820, filed on Apr. 8, 2016, entitled "METHODS TO SPECIFICALLY PROFILE PROTEASE ACTIVITY AT LYMPH NODES", the entire contents of each of which are incorporated herein by reference.

GOVERNMENT SUPPORT

This invention was made with Government support under R01 CA174795 awarded by the National Institutes of Health. The Government has certain rights in the invention.

REFERENCE TO A SEQUENCE LISTING SUBMITTED AS A TEXT FILE VIA EFS-WEB

The instant application contains a Sequence Listing which has been submitted in ASCII format via EFS-Web and is hereby incorporated by reference in its entirety. The ASCII file, created on Oct. 4, 2018 is named M065670383US01-SEQ-HCL.TXT and is 29,787 bytes in size.

FIELD

The present invention relates to methods and products associated with detecting and monitoring the activity of proteases in vivo using affinity assays. These methods and products form the basis of and may be used as an ultrasensitive diagnostic platform. The invention also relates to products, kits, and databases for use in the methods of the invention.

BACKGROUND

Detection of nascent, clinically occult metastases may significantly benefit patient outcomes, as approximately nine out of ten deaths from cancer are due to metastases. Generally, it remains the prognostic rule of thumb that local tumors are curable, while disseminated tumors are often not and require more stringent therapeutic interventions. An early step in metastatic progression often involves invasive growth of the primary tumor to proximal lymph nodes (LN).

Typically, lymph nodes (LN) are functionally probed via invasive surgical removal, which is associated with significant morbidity to patients. For example, patients and clinicians are often forced to proceed with aggressive LN extraction procedures without any information about the invasive nature of tumor cells, leading to unnecessary morbidity associated with surgeries. Currently, LN status is assessed via a combination of sentinel lymph node biopsy (whereby a dye is injected intratumorally and stained draining lymph nodes are presumed to be viable sites for metastasis) and imaging (including CT, PET and MRI). While these techniques can determine whether tumor cells are present, they fail to provide information regarding their metastatic potential. Furthermore, currently available diagnostic tools can also miss early metastatic events, which may lead to high relapse rates after surgeries for the primary tumor.

SUMMARY

In some aspects, the disclosure provides compositions and methods for detecting and monitoring the activity of proteases in vivo using affinity assays. The disclosure relates, in part, to the discovery that biomarker nanoparticles targeted to the lymph nodes of a subject are useful for the diagnosis and monitoring of certain medical conditions (e.g., metastatic cancer, infection with certain pathogenic agents). In some aspects, methods and compositions described by the disclosure are useful for monitoring of endogenous immune activity and efficacy of immunotherapies in causing an immune response.

Accordingly, in some aspects, the disclosure provides a composition comprising a lymph node biomarker nanoparticle, wherein the lymph node biomarker nanoparticle comprises a modular structure having a carrier domain linked to a lymph node specific enzyme susceptible detectable marker, wherein the enzyme susceptible detectable marker is comprised of a lymph node specific enzyme susceptible domain linked to a detectable marker whereby the detectable marker is capable of being released from the biomarker nanoparticle when exposed to an enzyme present in a lymph node.

In some aspects, the disclosure provides a method comprising administering to a subject a lymph node biomarker nanoparticle as described by the disclosure; analyzing a biological sample from the subject, wherein the biological sample is not a lymph node, and determining whether the detectable marker is in the biological sample, wherein the presence of the detectable marker in the biological sample is indicative of the enzyme being present in an active form within the lymph node of the subject. In some embodiments, the biological sample is urine.

In some aspects, the disclosure provides method comprising administering to the lymph node of a subject a lymph node biomarker nanoparticle, wherein the lymph node biomarker nanoparticle comprises a modular structure having a carrier domain linked to a lymph node specific enzyme susceptible detectable marker, wherein the lymph node specific enzyme susceptible detectable marker is comprised of an enzyme susceptible domain linked to a detectable marker whereby the detectable marker is capable of being released from the biomarker nanoparticle when exposed to an enzyme present in a lymph node; obtaining a urine sample from the subject for detection of the detectable marker; and, analyzing the urine sample using a capture assay in order to detect the presence of the detectable marker, wherein the presence of the detectable marker in the urine sample is indicative of the enzyme being present in an active form within a lymph node of the subject.

In some aspects, the disclosure provides a method for determining metastatic stage of a tumor comprising administering to the lymph node of a subject having a tumor a lymph node biomarker nanoparticle, wherein the lymph node biomarker nanoparticle comprises a modular structure having a carrier domain linked to a lymph node specific enzyme susceptible detectable marker, wherein the lymph node specific enzyme susceptible detectable marker is comprised of an enzyme susceptible domain linked to a detectable marker whereby the detectable marker is capable of being released from the biomarker nanoparticle when exposed to a metastatic tumor-associated enzyme in a lymph node; obtaining a urine sample from the subject for detection of the detectable marker; and, analyzing the urine sample using a capture assay in order to detect the presence of the detectable marker, wherein the presence of the detectable marker in the urine sample is indicative of the subject having a metastatic tumor.

In some aspects, the disclosure provides a method for identifying a pathogenic agent comprising administering to the lymph node of a subject infected or suspected of being infected with a pathogenic agent a lymph node biomarker nanoparticle, wherein the lymph node biomarker nanoparticle comprises a modular structure having a carrier domain linked to a lymph node specific enzyme susceptible detectable marker, wherein the lymph node specific enzyme susceptible detectable marker is comprised of an enzyme susceptible domain linked to a detectable marker whereby the detectable marker is capable of being released from the biomarker nanoparticle when exposed to an enzyme associated with a pathogenic agent; obtaining a urine sample from the subject for detection of the marker; and, analyzing the urine sample using a capture assay in order to detect the presence of the detectable marker, wherein the presence of the detectable marker in the urine sample is indicative of the subject being infected with the pathogenic agent.

In some embodiments, a lymph node biomarker nanoparticle is administered to a subject by systemic administration. In some embodiments, systemic administration of a lymph node biomarker nanoparticle results in delivery of the lymph node biomarker nanoparticle to the lymph node of a subject. In some embodiments, a lymph node biomarker nanoparticle is administered to a subject by injection. In some embodiments, the injection is subcutaneous injection.

In some embodiments, a carrier domain comprises a lymph node trafficking carrier. In some embodiments, the lymph node trafficking carrier is albumin, an albumin-binding peptide (e.g., sso7d), or a molecular amphiphile having high affinity to albumin. In some embodiments, the lymph node trafficking carrier is human serum albumin (HSA). In some embodiments, the HSA is recombinant HSA. In some embodiments, the lymph node trafficking carrier is an antibody. In some embodiments, the antibody is an antibody targeting DEC-205, mannose receptor, mannose binding lectin, ficolins, DC-SIGN, DCAR, DCIR, dectins, DLEC, scavenger receptors, F4/80, Fc receptor, or DC-STAMP.

In some embodiments, the lymph node trafficking carrier is a polymeric scaffold that is greater than 40 kDa. In some embodiments, the lymph node trafficking carrier is a nanoparticle that is between about 10 nm and about 50 nm in diameter. In some embodiments, the lymph node trafficking carrier is a high molecular weight protein. In some embodiments, a high molecular weight protein is greater than 40 kDa.

In some embodiments, a lymph node specific enzyme susceptible domain comprises a cancer substrate. In some embodiments, the lymph node specific enzyme susceptible domain comprises a metastatic cancer substrate. In some embodiments, the cancer substrate is a substrate for a protease selected from ADAM28, MMP9, and MMP12. In some embodiments, a lymph node specific enzyme susceptible domain comprises an immune-associated substrate. In some embodiments, the immune-associated substrate is a substrate for a protease selected from granzymes A, B, K and Cathepsin D. In some embodiments, the lymph node specific enzyme susceptible domain comprises a sequence selected from SEQ ID NO: 2-59.

In some embodiments, a lymph node biomarker nanoparticle is a multiplexed library of lymph node specific enzyme susceptible detectable markers. In some embodiments, the multiplexed library of lymph node specific enzyme susceptible detectable markers comprise 2, 5, 10, or more enzyme susceptible detectable markers.

In some embodiments, lymph node specific enzyme susceptible detectable markers are mass encoded protease substrates or ligand encoded protease substrates.

In some embodiments of methods described by the disclosure, the step of analyzing the biological sample (e.g., urine sample) detectable markers comprises identifying mass-encoded protease substrates using LC-MS/MS. In some embodiments, the step of analyzing the biological sample detectable markers comprises measuring fluorescence of the detectable markers, for example using spectrophotometry.

In some embodiments, an enzyme present in an active form within a lymph node (e.g., a lymph node specific enzyme that releases a detectable agent from a biomarker nanoparticle) is indicative of a metastatic cancer. In some embodiments, the enzyme present in an active form within the lymph node is indicative of an immune status indicating sensitivity to immune therapy.

Each of the embodiments of the invention can encompass various recitations made herein. It is, therefore, anticipated that each of the recitations of the invention involving any one element or combinations of elements can, optionally, be included in each aspect of the invention.

BRIEF DESCRIPTION OF DRAWINGS

FIG. 2A depicts one embodiment of multiplexed, mass-encoded substrate-reporter tandems (synthetic biomarkers') conjugated to serum albumin (e.g., human serum albumin; HSA) as a protein chaperone to the lymph node. FIG. 2B depicts subcutaneous injection (I) of a protein-chaperoned synthetic biomarker library results specifically in lymph node accumulation (arrows), where substrates are cleaved by their cognate proteases (II); reporter fragments (e.g., mass barcode(s)) enter the blood stream and are concentrated in the urine by filtering through the kidney, and disease signatures are quantified by LC-MS/MS (III).

FIG. 3A depicts patient data for primary melanoma (n=104) and regional lymph node metastatic (n=29) samples used to produce the fold expression data depicted in FIG. 3B. FIG. 3B shows fold expression data for a candidate protease "hit list", which includes proteases known to be involved in immune function (GZMK=Granzyme K; GZMA=Granzyme A) and cancer cell invasiveness (MMP9).

FIG. 4 A shows accumulation of albumin-conjugated synthetic biomarkers is highly selective for ipsilateral lymph node delivery (e.g., tumor-draining lymph nodes). FIG. 4B shows organ accumulation of albumin-conjugated synthetic biomarkers in various tissues (e.g., heart, lung, liver, spleen, kidney, and lymph nodes).

DETAILED DESCRIPTION

Aspects of the disclosure relate to methods and compositions for detecting and monitoring protease activity of lymph nodes as an indicator of certain disease states (e.g., metastatic cancers, infection with pathogenic agents, etc.). The disclosure relates, in some aspects, to the discovery that delivery of biomarker nanoparticles to the lymph nodes of a subject provides a minimally invasive snapshot of the state of immunity (e.g., tumor immunity) of the lymph node. Without wishing to be bound by any particular theory, synthetic biomarkers described herein can detect enzymatic activity in vivo and noninvasively quantify physiological processes by harnessing the capacity of the biomarker nanoparticles to circulate and sense the local microenvironment (e.g., lymph node environment) while providing a read-out (e.g., detection of a detectable marker) at a site that is remote (e.g., a urine sample) from the target tissue (e.g., lymph node).

For instance, as shown in the Example section described herein, lymph node specific protease activity can be assessed in order to determine the metastatic state of a tumor. In another example, lymph node specific protease activity can be assessed in order to determine whether a subject is infected with a pathogenic agent. Unlike other nanoparticle sensors that function by producing a localized signal, the compositions of the invention sense protease activity by releasing reporters locally at the sites of interest, i.e., in the lymph nodes, but then are filtered and detected remotely from the urine. By using distinct ligands and their cognate binding molecules, a panel of heterobifunctionalized reporters were also developed that can be detected using assays such as standardized 96-well plate assays, removing the need for mass spectrometry. This system is readily extensible by incorporating additional ligand-capture agent pairs and is amenable for detection by other methods including paper-based test strips(lateral flow assays) at the point of care, assays including bead-based assays (e.g., immunoprecipitation), surface plasmon resonance, nanoelectronics (e.g., nanowires) etc.

The compositions and methods of the disclosure have a number of advantages over the prior art methods. For example, current methods functionally probe lymph nodes (LN) via invasive surgical removal, which is associated with significant morbidity to patients. Less invasive imaging modalities can help determine whether tumor cells are present in the lymph node, but they fail to provide information regarding invasiveness or immune activity. In some aspects, the disclosure provides compositions and methods that addresses these issues. In some embodiments, the disclosure provides probes (e.g., biomarker nanoparticles) sensitive to proteases in the lymph node (LN) to accomplish this.

Figure 1:
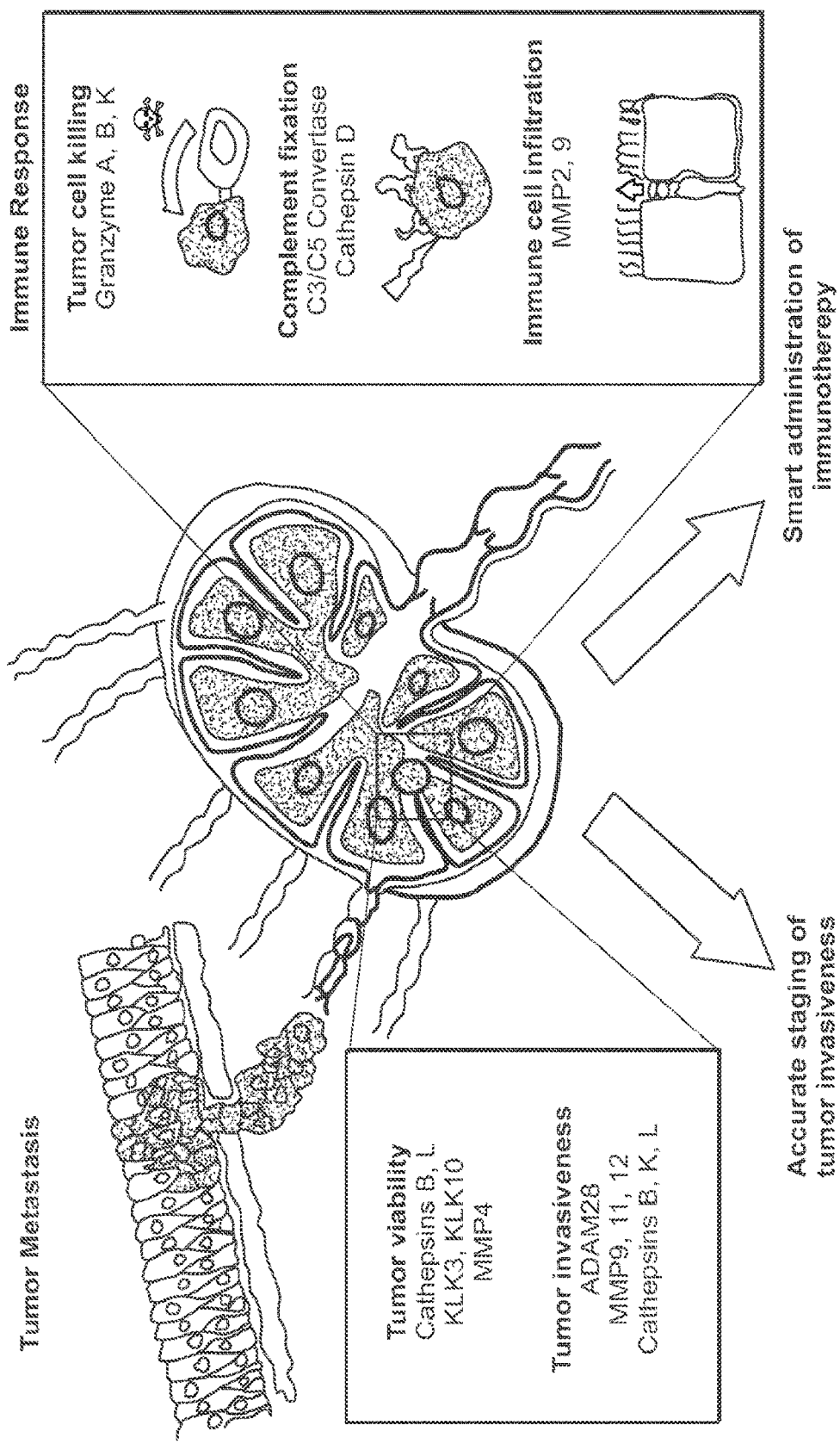
FIG. 1 demonstrate how lymph nodes are critical sites in the body for both tumor metastasis and immune response. Cancer cells from the primary tumor invade the lymph node and have different proteolytic landscapes than the primary tumor. Immune cells also utilize proteases to engage with target cells and also infiltrate into the lymph node. Profiling both axes of lymph node proteases will enable accurate tumor staging and inform immunotherapy regimens.

Aberrantly expressed proteases are candidate enzymes for cancer detection and analysis as they play critical roles in many cancers. Additionally, proteases are involved in many immune processes, including immune cell trafficking to and from the lymph node and target cell killing (FIG. 1). Accordingly, in some embodiments the disclosure relates to the delivery of a set of protease-sensitive substrates to the lymph node using lymph node specific trafficking carriers. Upon encountering their cognate proteases, peptide substrates are cleaved and reporter fragments are excreted into urine, providing anon-invasive diagnostic readout. In some embodiments, the delivered substrates are responsive to proteases enriched in different stages of tumor invasiveness (e.g., metastasis) and provide a high resolution, functionality driven snapshot of LN microenvironment (e.g., LN metastases).

Accordingly, in some aspects the disclosure provides a composition comprising a lymph node biomarker nanoparticle, wherein the lymph node biomarker nanoparticle comprises a modular structure having a carrier domain linked to a lymph node specific enzyme susceptible detectable marker, wherein the enzyme susceptible detectable marker is comprised of a lymph node specific enzyme susceptible domain linked to a detectable marker whereby the detectable marker is capable of being released from the biomarker nanoparticle when exposed to an enzyme present in a lymph node.

Carrier Domain

The biomarker nanoparticle comprises a modular structure having a carrier domain linked to an enzyme susceptible detectable marker. A modular structure, as used herein, refers to a molecule having multiple domains.

The carrier domain may include a single type of enzyme susceptible detectable marker, such as, a single type of enzyme susceptible domain and or detectable marker or it may include multiple type of enzyme susceptible detectable markers, such as, different enzyme susceptible domains and detectable markers. For instance each carrier may include 1 type of enzyme susceptible detectable marker or it may include 2-1,000 different enzyme susceptible detectable markers or any integer therebetween. Alternatively each carrier may include greater than 1,000 enzyme susceptible detectable markers. Multiple copies of the biomarker nanoparticle are administered to the subject. Some mixtures of biomarker nanoparticles may include enzyme susceptible detectable markers that are enzymes, others may be enzymatic susceptible domains, and other may be mixtures of the two. Additionally a plurality of different biomarker nanoparticles may be administered to the subject to determine whether multiple enzymes and/or substrates are present. In that instance, the plurality of different biomarker nanoparticles includes a plurality of detectable markers, such that each enzyme susceptible domain is associated with a particular detectable marker or molecules.

In some embodiments, the carrier domain comprises a lymph node trafficking carrier. As used herein, a "lymph node trafficking carrier" refers to a carrier (e.g., a protein, nucleic acid, or other molecule, such as a biological molecule or a nanoparticle) that enters the reticuloendothelial system (RES) and preferentially directs a biomarker nanoparticle to a lymph node of a subject. Examples of lymph node trafficking carriers include but are not limited to albumin, albumin-binding peptides (e.g., peptides having the core sequence DICLPRWGCLW (SEQ ID NO: 60), as disclosed by Dennis et al., J. Biol. Chem. 277, 35035-35043, (2002)), a molecular amphiphile having high affinity to albumin, or peptides based on an Sso7d scaffold (for example as disclosed by Traxlmayr et al. J. Biol. Chem. 291, 22496-22508, (2016)). In some embodiments, a lymph node trafficking carrier is injected into a subject and self-assembles with albumin in interstitial space of the subject, resulting in trafficking to the lymph nodes.

In some embodiments, a lymph node trafficking carrier is an antibody. For example, in some embodiments, a lymph node trafficking carrier comprises a HIV neutralizing antibody. Examples of HIV neutralizing antibodies include antibodies targeting MPER of gp41, V1V2-glycan, V3-glycan, and HIV CD4 binding site. In some embodiments, a lymph node trafficking carrier comprises a cancer-targeted antibody (e.g., monoclonal antibody). Examples of cancer-targeted antibodies include but are not limited to bevacizumab, cetuximab, ipilimumab, and brentuximab.

In some embodiments, a lymph node trafficking carrier is a protein having a molecular weight greater than 40 kDa, for example as disclosed by McLennan, Danielle N., Christopher J. H. Porter, and Susan A. Charman. "Subcutaneous Drug Delivery and the Role of the Lymphatics." Drug Discovery Today: Technologies 2, no. 1 (March 2005): 89-96. doi:10.1016/j.ddtec.2005.05.006. In some embodiments, a lymph node trafficking carrier is a non-protein-based (e.g., polymeric scaffold) that is greater than 40 kDa, or a nanoparticle that is between 10 nm and 50 nm in diameter. In some embodiments, the lymph node trafficking carrier is a high molecular weight protein or polymer, for example an Fc domain of an antibody, transthyretin, or a poly(ethylene glycol) polymer of a sufficient molecular weight (e.g., greater than 40 kDa).

The carrier domain may serve as the core of the nanoparticle. A purpose of the carrier domain is to serve as a platform for the enzyme susceptible detectable marker. As such, the carrier can be any material or size as long as it can serve as a carrier or platform. Preferably the material is non-immunogenic, i.e. does not provoke an immune response in the body of the subject to which it will be administered. Another purpose is that it may function as a targeting means to target the modular structure to a tissue, cell or molecule. In some embodiments the carrier domain is a particle. A particle, for example, a nanoparticle, may, for instance, result in passive targeting to tumors by circulation. Other types of carriers, include, for instance, compounds that cause active targeting to tissue, cells or molecules. Examples of carriers include, but are not limited to, microparticles, nanoparticles, aptamers, peptides (RGD, iRGD, LyP-1, CREKA, etc.), proteins, nucleic acids, polysaccharides, polymers, antibodies or antibody fragments (e.g., herceptin, cetuximab, panitumumab, etc.) and small molecules (e.g., erlotinib, gefitinib, sorafenib, etc.).

As used herein the term "particle" includes nanoparticles as well as microparticles. Nanoparticles are defined as particles of less than 1.0 µm in diameter. A preparation of nanoparticles includes particles having an average particle size of less than 1.0 µm in diameter. Microparticles are particles of greater than 1.0 µm in diameter but less than 1 mm. A preparation of microparticles includes particles having an average particle size of greater than 1.0 µm in diameter. The microparticles may therefore have a diameter of at least 5, at least 10, at least 25, at least 50, or at least 75 microns, including sizes in ranges of 5-10 microns, 5-15 microns, 5-20 microns, 5-30 microns, 5-40 microns, or 5-50 microns. A composition of particles may have heterogeneous size distributions ranging from 10 nm to mm sizes. In some embodiments the diameter is about 5 nm to about 500 nm. In other embodiments, the diameter is about 100 nm to about 200 nm. In other embodiment, the diameter is about 10 nm to about 100 nm.

The particles may be composed of a variety of materials including iron, ceramic, metallic, natural polymer materials (including lipids, sugars, chitosan, hyaluronic acid, etc.), synthetic polymer materials (including poly-lactide-coglycolide, poly-glycerol sebacate, etc.), and non-polymer materials, or combinations thereof.

The particles may be composed in whole or in part of polymers or non-polymer materials. Non-polymer materials, for example, may be employed in the preparation of the particles. Exemplary materials include alumina, calcium carbonate, calcium sulfate, calcium phosphosilicate, sodium phosphate, calcium aluminate, calcium phosphate, hydroxyapatite, tricalcium phosphate, dicalcium phosphate, tricalcium phosphate, tetracalcium phosphate, amorphous calcium phosphate, octacalcium phosphate, and silicates. In certain embodiments the particles may comprise a calcium salt such as calcium carbonate, a zirconium salt such as zirconium dioxide, a zinc salt such as zinc oxide, a magnesium salt such as magnesium silicate, a silicon salt such as silicon dioxide or a titanium salt such as titanium oxide or titanium dioxide. A number of biodegradable and non-biodegradable biocompatible polymers are known in the field of polymeric biomaterials, controlled drug release and tissue engineering (see, for example, U.S. Pat. Nos. 6,123,727; 5,804,178; 5,770,417; 5,736,372; 5,716,404 to Vacanti; U.S. Pat. Nos. 6,095,148; 5,837,752 to Shastri; U.S. Pat. No. 5,902,599 to Anseth; U.S. Pat. Nos. 5,696,175; 5,514,378; 5,512,600 to Mikos; U.S. Pat. No. 5,399,665 to Barrera; U.S. Pat. No. 5,019,379 to Domb; U.S. Pat. No. 5,010,167 to Ron; U.S. Pat. No. 4,946,929 to d'Amore; and U.S. Pat. Nos. 4,806,621; 4,638,045 to Kohn; see also Langer, Acc. Chem. Res. 33:94, 2000; Langer, J. Control Release 62:7, 1999; and Uhrich et al., Chem. Rev. 99:3181, 1999; all of which are incorporated herein by reference).

Polymers include, but are not limited to: polyamides, polycarbonates, polyalkylenes, polyalkylene glycols, polyalkylene oxides, polyalkylene terepthalates, polyvinyl alcohols, polyvinyl ethers, polyvinyl esters, polyvinyl halides, polyglycolides, polysiloxanes, polyurethanes and copolymers thereof, alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, cellulose sulphate sodium salt, poly(methyl methacrylate), poly(ethylmethacrylate), poly(butylmethacrylate), poly(isobutylmethacrylate), poly(hexlmethacrylate), poly(isodecylmethacrylate), poly(lauryl methacrylate), poly(phenyl methacrylate), poly(methyl acrylate), poly(isopropyl acrylate), poly(isobutyl acrylate), poly(octadecyl acrylate), polyethylene, polypropylene poly(ethylene glycol), poly (ethylene oxide), poly(ethylene terephthalate), poly(vinyl alcohols), poly(vinyl acetate, poly vinyl chloride and polystyrene.

Examples of non-biodegradable polymers include ethylene vinyl acetate, poly(meth) acrylic acid, polyamides, copolymers and mixtures thereof.

Examples of biodegradable polymers include synthetic polymers such as polymers of lactic acid and glycolic acid, polyanhydrides, poly(ortho)esters, polyurethanes, poly(butic acid), poly(valeric acid), poly(caprolactone), poly(hydroxybutyrate), poly(lactide-co-glycolide) and poly(lactide-co-caprolactone), and natural polymers such as alginate and other polysaccharides including dextran and cellulose, collagen, chemical derivatives thereof (substitutions, additions of chemical groups, for example, alkyl, alkylene, hydroxylations, oxidations, and other modifications routinely made by those skilled in the art), albumin and other hydrophilic proteins, zein and other prolamines and hydrophobic proteins, copolymers and mixtures thereof. In general, these materials degrade either by enzymatic hydrolysis or exposure to water in vivo, by surface or bulk erosion. The foregoing materials may be used alone, as physical mixtures (blends), or as co-polymers. In some embodiments the polymers are polyesters, polyanhydrides, polystyrenes, polylactic acid, polyglycolic acid, and copolymers of lactic and glycoloic acid and blends thereof.

PVP is a non-ionogenic, hydrophilic polymer having a mean molecular weight ranging from approximately 10,000 to 700,000 and the chemical formula $(C_6H_9NO)[n]$. PVP is also known as poly[1-(2-oxo-1-pyrrolidinyl)ethylene], Povidone™, Polyvidone™, RP 143™, Kollidon™, Peregal ST™, Periston™, Plasdone™, Plasmosan™, Protagent™, Subtosan™, and Vinisil™. PVP is non-toxic, highly hygroscopic and readily dissolves in water or organic solvents.

Polyethylene glycol (PEG), also known as poly(oxyethylene) glycol, is a condensation polymer of ethylene oxide and water having the general chemical formula $HO(CH_2CH_2O)[n]H$.

Polyvinyl alcohol (PVA) is a polymer prepared from polyvinyl acetates by replacement of the acetate groups with hydroxyl groups and has the formula $(CH_2CHOH)[n]$. Most polyvinyl alcohols are soluble in water.

PEG, PVA and PVP are commercially available from chemical suppliers such as the Sigma Chemical Company (St. Louis, Mo.).

In certain embodiments the particles may comprise poly (lactic-co-glycolic acid) (PLGA).

The carrier may be composed of inorganic materials. Inorganic materials include, for instance, magnetic materials, conductive materials, and semiconductor materials.

In addition to particles the carrier may be composed of any organic carrier, including biological and living carriers such as cells, viruses, bacteria, as well as any non-living organic carriers, or any composition enabling exposure of enzyme substrates to enzymes in disease (including extracellular, membrane-bound, and intracellular enzymes).

In some embodiments, the particles are porous. A porous particle can be a particle having one or more channels that extend from its outer surface into the core of the particle. In some embodiments, the channel may extend through the particle such that its ends are both located at the surface of the particle. These channels are typically formed during synthesis of the particle by inclusion followed by removal of a channel forming reagent in the particle.

The size of the pores may depend upon the size of the particle. In certain embodiments, the pores have a diameter of less than 15 microns, less than 10 microns, less than 7.5 microns, less than 5 microns, less than 2.5 microns, less than 1 micron, less than 0.5 microns, or less than 0.1 microns. The degree of porosity in porous particles may range from greater than 0 to less than 100% of the particle volume. The degree of porosity may be less than 1%, less than 5%, less than 10%, less than 15%, less than 20%, less than 25%, less than 30%, less than 35%, less than 40%, less than 45%, or less than 50%. The degree of porosity can be determined in a number of ways. For example, the degree of porosity can be determined based on the synthesis protocol of the carriers (e.g., based on the volume of the aqueous solution or other channel-forming reagent) or by microscopic inspection of the carriers post-synthesis.

The plurality of particles may be homogeneous for one or more parameters or characteristics. A plurality that is homogeneous for a given parameter, in some instances, means that particles within the plurality deviate from each other no more than about +/−10%, preferably no more than about +/−5%, and most preferably no more than about +/−1% of a given quantitative measure of the parameter. As an example, the particles may be homogeneously porous. This means that the degree of porosity within the particles of the plurality differs by not more than +/−10% of the average porosity. In other instances, a plurality that is homogeneous means that all the particles in the plurality were treated or processed in the same manner, including for example exposure to the same agent regardless of whether every particle ultimately has all the same properties. In still other embodiments, a plurality that is homogeneous means that at least 80%, preferably at least 90%, and more preferably at least 95% of particles are identical for a given parameter.

The plurality of particles may be heterogeneous for one or more parameters or characteristics. A plurality that is heterogeneous for a given parameter, in some instances, means that particles within the plurality deviate from the average by more than about +/−10%, including more than about +/−20%. Heterogeneous particles may differ with respect to a number of parameters including their size or diameter, their shape, their composition, their surface charge, their degradation profile, whether and what type of agent is comprised by the particle, the location of such agent (e.g., on the surface or internally), the number of agents comprised by the particle, etc. The invention contemplates separate synthesis of various types of particles which are then combined in any one of a number of pre-determined ratios prior to contact with the sample. As an example, in one embodiment, the particles may be homogeneous with respect to shape (e.g., at least 95% are spherical in shape) but may be heterogeneous with respect to size, degradation profile and/or agent comprised therein.

Particle size, shape and release kinetics can also be controlled by adjusting the particle formation conditions. For example, particle formation conditions can be optimized to produce smaller or larger particles, or the overall incubation time or incubation temperature can be increased, resulting in particles which have prolonged release kinetics.

The particles may also be coated with one or more stabilizing substances, which may be particularly useful for long term depoting with parenteral administration or for oral delivery by allowing passage of the particles through the stomach or gut without dissolution. For example, particles intended for oral delivery may be stabilized with a coating of a substance such as mucin, a secretion containing mucopolysaccharides produced by the goblet cells of the intestine, the submaxillary glands, and other mucous glandular cells.

To enhance delivery the particles may be incorporated, for instance, into liposomes, virosomes, cationic lipids or other lipid based structures. The term "cationic lipid" refers to lipids which carry a net positive charge at physiological pH. Such lipids include, but are not limited to, DODAC, DOTMA, DDAB, DOTAP, DC-Chol and DMRIE. Additionally, a number of commercial preparations of cationic lipids are available. These include, for example, LIPOFECTIN® (commercially available cationic liposomes comprising DOTMA and DOPE, from GIBCO/BRL, Grand Island, N.Y., USA); LIPOFECTAMINE® (commercially available cationic liposomes comprising DOSPA and DOPE, from GIBCO/BRL); and TRANSFECTAM® (commercially available cationic lipids comprising DOGS in ethanol from Promega Corp., Madison, Wis., USA). A variety of methods are available for preparing liposomes e.g., U.S. Pat. Nos. 4,186,183, 4,217,344, 4,235,871, 4,261,975, 4,485,054, 4,501,728, 4,774,085, 4,837,028, 4,946,787; and PCT Publication No. WO 91/17424. The particles may also be composed in whole or in part of GRAS components. i.e., ingredients are those that are Generally Regarded As Safe (GRAS) by the US FDA. GRAS components useful as particle material include non-degradable food based particles such as cellulose.

The carrier domain can serve several functions. As discussed above, it may be useful for targeting the product to a specific region, such as a tissue. In that instance it could include a targeting agent such as a glycoprotein, an antibody, or a binding protein.

Further, the size of the carrier domain may be adjusted based on the particular use of the biomarker nanoparticle. For instance, the carrier domain may be designed to have a size greater than 5 nm. Particles, for instance, of greater than 5 nm are not capable of entering the urine, but rather, are cleared through the reticuloendothelial system (RES; liver, spleen, and lymph nodes). By being excluded from the removal through the kidneys any uncleaved biomarker nanoparticle will not be detected in the urine during the analysis step. Additionally, larger particles can be useful for maintaining the particle in the blood or in a tumor site where large particles are more easily shuttled through the vasculature. In some embodiments the carrier domain is 500 microns-5 nm, 250 microns-5 nm, 100 microns-5 nm, 10 microns-5 nm, 1 micron-5 nm, 100 nm-5 nm, 100 nm-10 nm, 50 nm-10 nm or any integer size range therebetween. In other instances the carrier domain is smaller than 5 nm in size. In such instance the biomarker nanoparticle will be cleared into the urine. However, the presence of free detectable marker can still be detected for instance using mass spectrometry. In some embodiments the carrier domain is 1-5 nm, 2-5 nm, 3-5 nm, or 4-5 nm.

Optionally the carrier domain may include a biological agent. In one embodiment a biological agent could be incorporated in the carrier domain or it may make up the carrier domain. For instance, it may form the scaffold or platform that the proteolytic domain is attached to. Thus the compositions of the invention can achieve two purposes at the same time, the diagnostic methods and delivery of a therapeutic agent. In some embodiments the biological agent may be an enzyme inhibitor. In that instance the biological agent can inhibit proteolytic activity at a local site and the detectable marker can be used to test the activity of that particular therapeutic at the site of action. HIV is an example of the disease in which active proteases can be monitored. In this embodiment the composition may include a microparticle or other delivery device carrying a protease inhibitor. The protease susceptible site may be sensitive to the HIV proteases such that feedback can be provided regarding the activity of the particular protease inhibitor.

Enzyme Susceptible Detectable Markers

The enzyme susceptible detectable marker is a portion of the modular structure that is connected to the carrier. An enzyme susceptible detectable marker, as used herein, is the portion of the modular structure that promotes the enzymatic reaction in the subject, causing the release of a detectable marker. The enzyme susceptible detectable marker is an enzyme susceptible domain linked to a detectable marker.

The enzyme susceptible site is dependent on enzymes that are active in a specific disease state. For instance, tumors are associated with a specific set of enzymes. If the disease state being analyzed is a tumor then the product is designed with an enzyme susceptible site that matches that of the enzyme expressed by the tumor or other diseased tissue. Alternatively, the enzyme specific site may be associated with enzymes that are ordinarily present but are absent in a particular disease state. In this example, a disease state would be associated with a lack or signal associated with the enzyme, or reduced levels of signal compared to a normal reference.

An enzyme, as used herein refers to any of numerous proteins produced in living cells that accelerate or catalyze the metabolic processes of an organism. Enzymes act on substrates. The substrate binds to the enzyme at a location called the active site just before the reaction catalyzed by the enzyme takes place. Enzymes include but are not limited to proteases, glycosidases, lipases, heparinases, phosphatases.

In some embodiments, an enzyme susceptible detectable marker comprises a substrate for a protease (e.g., an amino acid sequence that is cleaved by a protease). In some embodiments, the protease substrate is a substrate of a serine protease, cysteine protease, threonine protease, aspartic protease, glutamic protease, or a metalloprotease. Examples of serine protease substrates include but are not limited to SLKRYGGG (SEQ ID NO: 61; plasma kallikrein) and AAFRSRGA (SEQ ID NO: 62; kallikrein 1). Examples of cysteine protease substrates include but are not limited to xxFRFFxx (SEQ ID NO: 63; cathepsin B), QSVGFA (SEQ ID NO: 64; cathepsin B), and LGLEGAD (SEQ ID NO: 65; cathepsin K). A non-limiting example of a theronine protease substrate is GPLD (SEQ ID NO: 66; subunit beta 1c). Examples of aspartic protease substrates include but are not limited to LGVLIV (SEQ ID NO: 67; cathepsin D) and GLVLVA (SEQ ID NO: 68; cathepsin E. Examples of metalloprotease substrates include but are not limited to PAALVG (SEQ ID NO: 69; MMP2) and GPAGLAG (SEQ ID NO: 70; MMP9).

The enzyme susceptible site may be optimized to provide both high catalytic activity (or other enzymatic activity) for specified target enzymes but to also release optimized detectable markers for detection. Patient outcome depends on the phenotype of individual diseases at the molecular level, and this is often reflected in expression of enzymes. The recent explosion of bioinformatics has facilitated exploration of complex patterns of gene expression in human tissues (Fodor, S. A. Massively parallel genomics. Science 277, 393-395 (1997)). Sophisticated computer algorithms have been recently developed capable of molecular diagnosis of tumors using the immense data sets generated by expression profiling (Khan J, Wei J S, Ringner M, Saal L H, Ladanyi M, Westermann F, et al. Classification and diagnostic prediction of cancers using gene expression profiling and artificial neural networks. Nat Med 2001; 7:673-679.). This information can be accessed in order to identify enzymes and substrates associated with specific diseases. Based on this information the skilled artisan can identify appropriate enzyme or substrates to incorporate into the biomarker nanoparticle.

Table 1 provides a non-limiting list of enzymes associated with (either increased or decreased with respect to normal) disease and in some instances, the specific substrate. Table 2 provides a non-limiting list of substrates associated with disease or other conditions. Numerous other enzyme/substrate combinations associated with specific diseases or conditions are known to the skilled artisan and are useful according to the invention.

TABLE 1

| Disease | Enzyme | Substrate |
| --- | --- | --- |
| Cancer | MMP | collagens, gelatin, various ECM proteins |

TABLE 1-continued

| Disease | Enzyme | Substrate |
|---|---|---|
| Cancer | MMP-2 | type IV collagen and gelatin |
| Cancer | MMP-9 | type IV and V collagens and gelatin |
| Cancer | kallikreins | kininogens, plasminogen |
| Cancer | cathepsins | broad spectrum of substrates |
| Cancer | plasminogen activator, tPA | Plasminogen |
| Cancer | ADAM (A Diseintegrin And Metalloprotease, also MDC, Adamalysin) | various extracellular domains of transmembrane proteins |
| Pancreatic carcinoma | MMP-7 | various, e.g. collagen 18, FasL, HLE, DCN, IGFBP-3, MAG, plasminogen, other MMPs |
| Pancreatic Cancer | ADAM9, ADAM15 | various extracellular domains of transmembrane proteins |
| Prostate adenocarcinoma | Matriptase, a type II transmembrane serine protease | unspecific, cleaves after Lys or Arg residues |
| Prostate cancer | Kallikrein 3 | kininogens, plasminogen |
| Prostate cancer | ADAM15 | various extracellular domains of transmembrane proteins |
| Ovarian carcinoma | Kallikrein 6 | kininogens, plasminogen |
| Epithelial-derived tumors (breast, prostate, ovarian, colon, oral) | Matriptase, a type II transmembrane serine protease | unspecific, cleaves after Lys or Arg residues |
| Ovarian Cancer | MMP-2, MMP-9, kallikrein-10 (hk-10) | type IV and V collagens and gelatin, kininogens, plasminogen |
| Breast, gastric, prostate cancer | cathepsins B, L and D | broad spectrum of substrates |
| Endometrial cancer | cathepsin B | unspecific cleavage of a broad spectrum of substrates without clear sequence specificity |
| esophageal adenocarcinoma | cathepsin B | unspecific cleavage of a broad spectrum of substrates without clear sequence specificity |
| Invasive cancers, metastases | type II integral serine proteases (dipeptidyl peptidase IV (DPP4/CD26), seprase/fibroblast activation protein alpha (FAPalpha) and related type II transmembrane prolyl serine peptidases)) | |
| Invasive cancers, metastases | Seprase | various ECM proteins |
| Viral Infections | | |
| All Retroviruses | viral protease | precursor GagPol fusion |
| HIV | HIV protease (HIV PR, an aspartic protease) | precursor Gag and GagPol proteins |
| Hepatitis C | NS3 serine protease | viral precursor polyprotein |
| Dengue | Dengue protease | auocleavage (NS2B/NS3), NS3/NS4A and NS4B/NS5 cleavage |
| West Nile | NS2B/NS3pro | viral precursor polyprotein |
| Bacterial Infections | | |
| *Legionella* spp. | zinc metalloprotease | Me-Arg-Pro-Tyr |
| Meninogencephalitis | histolytic cysteine protease | |
| *Streptococcus pyogenes* (Group A *Streptococcus*) | streptococcal pyrogenic exotoxin B (SpeB) | extracellular matrix, immunoglobulins, complement components |
| *Clostridium difficile* | Cwp84 | fibronectin, laminin, vitronectin and other ECM proteins |
| Alzheimer's disease | BACE-1,2 (Alzheimer secretase) | β-amyloid precursor protein |
| Stroke and recovery cardiovascular disease | MMP, tPA Angiotensin Converting Enzyme (ACE) | angiotensin I, bradykinin |
| Atherosclerosis | cathepsin K, L, S | broad spectrum of substrates |
| arthritis | MMP-1 | triple-helical fibrillar collagens |
| rheumatoid arthritis | thrombin | Osteopontin |
| osteoarthritis | thrombin | Osteopontin |
| osteoporosis/ osteoarthritis | cathepsin K, S | broad spectrum of substrates |
| Arthritis, inflammatory joint disease | Aggrecanase (ADAMTS4, ADAMTS11) | aggrecans (proteoglycans) |
| thrombosis | factor Xa (thrombokinase) | Prothrombin |
| thrombosis | ADAMTS13 | von Willebrand factor (vWF) |
| thrombosis | plasminogen activator, tPA | Plasminogen |
| Stress-induced Renal pressure natriuresis | Prostasin | epithelial Na channel subunits |

TABLE 2

| DISEASE | TARGET SUBSTRATE | ENZYME |
|---|---|---|
| Inflammation | Interleukin 1 beta | MMP-2, MMP-3, MMP-9, Trypsin, chymotrypsin, pepsin, Lys-C, Glu-C, Asp-N, Arg-C |
| Pituitary gland dysfunction, abnormal bone density, growth disorders | IGFBP-3 | MMP-1, MMP-3, MMP-9, Trypsin, chymotrypsin, pepsin, Lys-C, Glu-C, Asp-N, Arg-C |

TABLE 2-continued

| DISEASE | TARGET SUBSTRATE | ENZYME |
|---|---|---|
| Cancer | TGF-beta | MMP-9, Trypsin, chymotrypsin, pepsin, Lys-C, Glu-C, Asp-N, Arg-C |
| Cancer, autoimmune disease | TNF | MMP-7, Trypsin, chymotrypsin, pepsin, Lys-C, Glu-C, Asp-N, Arg-C |
| Cancer, autoimmune disease | FASL | MMP-7, Trypsin, chymotrypsin, pepsin, Lys-C, Glu-C, Asp-N, Arg-C |
| Wound healing, cardiac disease | HB-EGF | MMP-3, Trypsin, chymotrypsin, pepsin, Lys-C, Glu-C, Asp-N, Arg-C |
| Pfeiffer syndrome | FGFR1 | MMP-2, Trypsin, chymotrypsin, pepsin, Lys-C, Glu-C, Asp-N, Arg-C |
| Cancer | Decorin | MMP-2, MMP-3, MMP-7, Trypsin, chymotrypsin, pepsin, Lys-C, Glu-C, Asp-N, Arg-C |
| Cancer | Tumor associated carbohydrate antigens | Endoglycosidases |
| Cancer | Sialyl Lewis$^a$ | O-glycanase |
| Cancer | Sialyl Lewis$^x$ | O-glycanase |
| Cancer/ Rheumatoid Arthritis, pulmonary hypertension | VEGF | Trypsin, chymotrypsin, pepsin, Lys-C, Glu-C, Asp-N, Arg-C |
| Cancer | EGF | Trypsin, chymotrypsin, pepsin, Lys-C, Glu-C, Asp-N, Arg-C |
| Cancer | IL2 | Trypsin, chymotrypsin, pepsin, Lys-C, Glu-C, Asp-N, Arg-C |
| Cancer inflammation/ angiogenesis | IL6 | Trypsin, chymotrypsin, pepsin, Lys-C, Glu-C, Asp-N, Arg-C |
| Cancer | IFN-γ | Trypsin, chymotrypsin, pepsin, Lys-C, Glu-C, Asp-N, Arg-C |
| Cancer inflammation/ angiogenesis, Rheumatoid Arthritis | TNF-α | Trypsin, chymotrypsin, pepsin, Lys-C, Glu-C, Asp-N, Arg-C |
| Cancer, Pulmonary fibrosis, Asthma | TGF-β | Trypsin, chymotrypsin, pepsin, Lys-C, Glu-C, Asp-N, Arg-C |
| Cancer, Pulmonary hypertension | PDGF | Trypsin, chymotrypsin, pepsin, Lys-C, Glu-C, Asp-N, Arg-C |
| Cancer, pulmonary cystadenoma | Fibroblast growth factor (FGF) | Trypsin, chymotrypsin, pepsin, Lys-C, Glu-C, Asp-N, Arg-C |
| Cancer | Brain-derived neurotrophic factor (BDNF) | Trypsin, chymotrypsin, pepsin, Lys-C, Glu-C, Asp-N, Arg-C |
| Cancer | Interferon regulatory factors (IRF-1, IRF-2) | Trypsin, chymotrypsin, pepsin, Lys-C, Glu-C, Asp-N, Arg-C |
| Inhibitor of tumor suppressors | MIF | Trypsin, chymotrypsin, pepsin, Lys-C, Glu-C, Asp-N, Arg-C |
| Lymphomas/ carcinomas, alveolar proteinosis | GM-CSF | Trypsin, chymotrypsin, pepsin, Lys-C, Glu-C, Asp-N, Arg-C |
| Cancer invasion | M-CSF | Trypsin, chymotrypsin, pepsin, Lys-C, Glu-C, Asp-N, Arg-C |
| Chemical carcinogenesis, multiple sclerosis, rheumatoid arthritis, Crohn's disease | IL-12 | Trypsin, chymotrypsin, pepsin, Lys-C, Glu-C, Asp-N, Arg-C |
| Natural Killer T cell leukemias, inflammatory bowel disease, rheumatoid arthritis | IL-15 | Trypsin, chymotrypsin, pepsin, Lys-C, Glu-C, Asp-N, Arg-C |
| Cirrhosis | Tissue inhibitor of MMPs (TIMPs) | Trypsin, chymotrypsin, pepsin, Lys-C, Glu-C, Asp-N, Arg-C |
| Cirrhosis | Collagen I, III | MMP-1, MMP-8, Trypsin, chymotrypsin, pepsin, Lys-C, Glu-C, Asp-N, Arg-C |
| Cirrhosis | Collagen IV, V | MMP-2, Trypsin, chymotrypsin, pepsin, Lys-C, Glu-C, Asp-N, Arg-C |

In some embodiments, the enzyme susceptible domain is a lymph node specific enzyme susceptible domain. As used herein, "lymph node specific enzyme susceptible domain" refers to an enzyme susceptible domain that is capable of being cleaved by a protease that is present (or upregulated) in a lymph node of a subject having a disease (e.g., cancer, metastatic cancer, an infection with a pathogenic agent, etc.). For example, certain cancers (e.g. metastatic cancers) are associated with upregulation of specific enzymes (e.g. ADAM28, MMP9, MMP12, ACE, C2, ADAMTSS, HTRA4, MMP16, etc.) in lymph nodes. In some embodiments, the lymph node specific enzyme susceptible domain comprises a cancer substrate, such as a metastatic cancer substrate. Examples of cancer substrates include but are not limited to substrates targeted by ADAM28, MMP9, MMP12, ACE, C2, ADAMTSS, HTRA4, or MMP16.

In some embodiments the enzyme susceptible detectable marker is a peptide that is susceptible to cleavage by an enzyme or causes cleavage of a substrate associated with a disease or condition. In some embodiments, the lymph node specific enzyme susceptible domain comprises an immune-associated substrate. Examples of immune-associated substrates include substrates for proteases such as granzymes A (e.g., ASPRAGGK; SEQ ID NO: 71), B (e.g., YEADSLEE;

SEQ ID NO: 72), K (e.g., YQYRAL; SEQ ID NO: 73), and Cathepsin D (LGVLIV; SEQ ID NO: 67).

An enzyme susceptible detectable marker may be attached directly to the carrier. For instance it may be coated directly on the surface of microparticles using known techniques. Alternatively if the carrier is a protein material it may be directly connected through a peptide bond. Additionally, the enzyme susceptible detectable marker may be connected to the carrier domain through the use of a linker. As used herein "linked" or "linkage" means two entities are bound to one another by any physicochemical means. Any linkage known to those of ordinary skill in the art, covalent or non-covalent, is embraced. Thus, in some embodiments the carrier has a linker attached to an external surface, which can be used to link the enzyme susceptible detectable marker. Another molecule can also be attached to the linker. In some embodiments, two molecules are linked using a transpeptidase, for example Sortase A.

The enzyme susceptible detectable marker is preferably a polymer made up of a plurality of chemical units. A "chemical unit" as used herein is a building block or monomer which may be linked directly or indirectly to other building blocks or monomers to form a polymer.

Detectable Markers

The detectable marker is capable of being released from the biomarker nanoparticle when exposed to an enzyme in vivo. The detectable marker once released is free to travel to a remote site for detection. A remote site is used herein to refer to a site in the body that is distinct from the bodily tissue housing the enzyme where the enzymatic reaction occurs. In some embodiments, the bodily tissue housing the enzyme where the enzymatic reaction occurs is a lymph node.

Modification of the enzyme susceptible domain by an enzyme in vivo, results in the production of a detectable marker. Alternatively, when the enzyme susceptible detectable marker is an enzyme the enzyme cleaves an endogenous substrate producing a detectable marker from the endogenous substrate. The detectable marker is a detectable molecule. It can be part of the enzyme susceptible domain, e.g. the piece that is released or added upon cleavage or it can be a separate entity. Preferably the detectable marker is composed of two ligands joined by a linker, as described above. The detectable marker may be comprised of, for instance one or more of a peptide, nucleic acid, small molecule, fluorophore/quencher, carbohydrate, particle, radiolabel, MRI-active compound, inorganic material, organic material, with encoded characteristics to facilitate optimal detection.

In some embodiments, a lymph node specific enzyme susceptible detectable marker comprises a capture ligand is a molecule that is capable of being captured by a binding partner. The detection ligand is a molecule that is capable of being detected by any of a variety of methods. While the capture ligand and the detection ligand will be distinct from one another in a particular detectable marker, the class of molecules that make us capture and detection ligands overlap significantly. For instance, many molecules are capable of being captured and detected. In some instances these molecules may be detected by being captured or capturing a probe. The capture and detection ligand each independently may be one or more of the following: a protein, a peptide, a polysaccharide, a nucleic acid, a fluorescent molecule, or a small molecule, for example. In some embodiments the detection ligand or the capture ligand may be, but is not limited to, one of the following: Alexa488, TAMRA, DNP, fluorescein, Oregon Green, Texas Red, Dansyl, BODIPY, Alexa405, Cascade Blue, Lucifer Yellow, Nitrotyrosine, HA-tag, FLAG-tag, His-tag, Myc-tag, V5-tag, S-tag, biotin or streptavidin. In some embodiments, the capture ligand and a detection ligand are connected by a linker. The purpose of the linker is prevent steric hindrance between the two ligands. Thus, the linker may be any type of molecule that achieves this. The linker may be, for instance, a polymer such as PEG, a protein, a peptide, a polysaccharide, a nucleic acid, or a small molecule. In some embodiments the linker is a protein of 10-100 amino acids in length. In other embodiments the linker is GluFib (SEQ ID NO: 1). Optionally, the linker may be 8 nm-100 nm, 6 nm-100 nm, 8 nm-80 nm, 10 nm-100 nm, 13 nm-100 nm, 15 nm-50 nm, or 10 nm-50 nm in length.

In some embodiments, the detectable marker is a ligand encoded reporter. Without wishing to be bound by any particular theory, a ligand encoded reporter binds to a target molecule (e.g., a target molecule present in a lymph node), allowing for detection of the target molecule at a site remote from where the ligand encoded reporter bound to the target (e.g., at a sight remote from a lymph node). In some embodiments, a ligand encoded reporter binds to a target molecule associated with a pathogenic agent. As used herein, "pathogenic agent" refers to a molecule that is indicative of the presence of a particular infectious agent (e.g., a virus, bacterium, parasite, etc.). Examples of pathogenic agents include viral proteins, bacterial proteins, biological toxins, and parasite-specific proteins (e.g., *S. mansoni* OVA protein).

In some embodiments, a detectable marker is a mass encoded reporter, for example an iCORE as described in WO2012/125808, filed Mar. 3, 2012, the entire contents of which are incorporated herein by reference. Upon arrival in the diseased microenvironment, the iCORE agents interface with aberrantly active proteases to direct the cleavage and release of surface-conjugated, mass-encoded peptide substrates into host urine for detection by mass spectrometry (MS) as synthetic biomarkers of disease.

The detectable marker may be detected by any known detection methods to achieve the capture/detection step. A variety of methods may be used, depending on the nature of the detectable marker. Detectable markers may be directly detected, following capture, through optical density, radioactive emissions, nonradiative energy transfers, or detectable markers may be indirectly detected with antibody conjugates, affinity columns, streptavidin-biotin conjugates, PCR analysis, DNA microarray, and fluorescence analysis.

The capture assay in some embodiments involves a detection step selected from the group consisting of an ELISA, including fluorescent, colorimetric, bioluminescent and chemiluminescent ELISAs, a paper test strip or LFA, bead-based fluorescent assay, and label-free detection, such as surface plasmon resonance (SPR). The capture assay may involve, for instance, binding of the capture ligand to an affinity agent.

The analysis step may be performed directly on the biological sample or the signature component may be purified to some degree first. For instance, a purification step may involve isolating the detectable marker from other components in the biological sample. Purification steps include methods such as affinity chromatography. As used herein an "isolated molecule" or "purified molecule" is a detectable marker that is isolated to some extent from its natural environment. The isolated or purified molecule need not be 100% pure or even substantially pure prior to analysis.

The methods for analysing detectable markers by identifying the presence of a detectable marker may be used to provide a qualitative assessment of the molecule (e.g., whether the detectable marker is present or absent) or a quantitative assessment (e.g., the amount of detectable marker present to indicate a comparative activity level of the enzymes. The quantitative value may be calculated by any means, such as, by determining the percent relative amount of each fraction present in the sample. Methods for making these types of calculations are known in the art.

The detectable marker may be labeled. For example, a label may be added directly to a nucleic acid when the isolated detectable marker is subjected to PCR. For instance, a PCR reaction performed using labeled primers or labeled nucleotides will produce a labeled product. Labeled nucleotides (e.g., fluorescein-labeled CTP) are commercially available. Methods for attaching labels to nucleic acids are well known to those of ordinary skill in the art and, in addition to the PCR method, include, for example, nick translation and end-labeling.

Labels suitable for use in the methods of the present invention include any type of label detectable by standard means, including spectroscopic, photochemical, biochemical, electrical, optical, or chemical methods. Preferred types of labels include fluorescent labels such as fluorescein. A fluorescent label is a compound comprising at least one fluorophore. Commercially available fluorescent labels include, for example, fluorescein phosphoramidides such as fluoreprime (Pharmacia, Piscataway, N.J.), fluoredite (Millipore, Bedford, Mass.), FAM (ABI, Foster City, Calif.), rhodamine, polymethadine dye derivative, phosphores, Texas red, green fluorescent protein, CY3, and CY5. Polynucleotides can be labeled with one or more spectrally distinct fluorescent labels. "Spectrally distinct" fluorescent labels are labels which can be distinguished from one another based on one or more of their characteristic absorption spectra, emission spectra, fluorescent lifetimes, or the like. Spectrally distinct fluorescent labels have the advantage that they may be used in combination ("multiplexed"). Radionuclides such as 3H, 125I, 35S, 14C, or 32P are also useful labels according to the methods of the invention. A plurality of radioactively distinguishable radionuclides can be used. Such radionuclides can be distinguished, for example, based on the type of radiation (e.g. $\alpha$, $\beta$, or $\delta$ radiation) emitted by the radionuclides. The 32P signal can be detected using a phosphoimager, which currently has a resolution of approximately 50 microns. Other known techniques, such as chemiluminescence or colormetric (enzymatic color reaction), can also be used.

Quencher compositions in which a "donor" fluorophore is joined to an "acceptor" chromophore by a short bridge that is the binding site for the enzyme may also be used. The signal of the donor fluorophore is quenched by the acceptor chromophore through a process believed to involve resonance energy transfer (RET). Cleavage of the peptide results in separation of the chromophore and fluorophore, removal of the quench, and generation of a subsequent signal measured from the donor fluorophore.

The disease or condition assessed according to the methods of the invention is any disease or condition that is associated with an enzyme. For instance, cancer, cardiovascular disease, arthritis, viral, bacterial, parasitic or fungal infection, Alzheimer's disease emphysema, thrombosis, hemophilia, stroke, organ dysfunction, any inflammatory condition, vascular disease, parenchymal disease, or a pharmacologically-induced state are all known to be associated with enzymes. A pharmacologically induced state is a condition in which enzyme inhibitors and other agents directly or indirectly affect enzyme activities. Thus each of the these can be assessed or monitored or studied according to methods of the invention.

Methods

It is useful to be able to differentiate non-metastatic primary tumors from metastatic tumors, because metastasis is a major cause of treatment failure in cancer patients. If metastasis can be detected early, it can be treated aggressively in order to slow the progression of the disease. Metastasis is a complex process involving detachment of cells from a primary tumor, movement of the cells through the circulation, and eventual colonization of tumor cells at local or distant tissue sites. Additionally, it is desirable to be able to detect a predisposition for development of a particular cancer such that monitoring and early treatment may be initiated. For instance, an extensive cytogenetic analysis of hematologic malignancies such as lymphomas and leukemias have been described, see e.g., Solomon et al., Science 254, 1153-1160, 1991. Early detection or monitoring using the non-invasive methods of the invention may be useful.

Solid tumors progress from tumorigenesis through a metastatic stage and into a stage at which several different active proteases can be involved. Some protease are believed to alter the tumor such that it can progress to the next stage, i.e., by conferring proliferative advantages, the ability to develop drug resistance or enhanced angiogenesis, proteolysis, or metastatic capacity.

Accordingly, in some aspects, the disclosure provides a method for determining metastatic stage of a tumor comprising administering to the lymph node of a subject having a tumor a lymph node biomarker nanoparticle, wherein the lymph node biomarker nanoparticle comprises a modular structure having a carrier domain linked to a lymph node specific enzyme susceptible detectable marker, wherein the lymph node specific enzyme susceptible detectable marker is comprised of an enzyme susceptible domain linked to a detectable marker whereby the detectable marker is capable of being released from the biomarker nanoparticle when exposed to a metastatic tumor-associated enzyme in a lymph node; obtaining a urine sample from the subject for detection of the detectable marker; and, analyzing the urine sample using a capture assay in order to detect the presence of the detectable marker, wherein the presence of the detectable marker in the urine sample is indicative of the subject having a metastatic tumor.

In addition to harboring nascent metastases, the LN is the site of numerous immune processes that have proven to be critical to anti-tumor therapies. For example, an emerging paradigm in oncology is the use of immunotherapies, whereby a patient's own immune system is directed against the tumor. Checkpoint blockade inhibitors and anti-tumor monoclonal antibodies have proven to be remarkably effective in the clinic for a diverse array of indications, and will likely become incorporated in standard of care for oncology. Anti-tumor immune responses are orchestrated in the tumor-draining LN, the same nodes that harbor metastases, which contain a trove of immunological activity. Thus, in some embodiments, an enzyme susceptible domain linked to a detectable marker releases the detectable marker when exposed to an enzyme associated with an anti-tumor response (e.g., an anti-tumor response resulting from treatment with a checkpoint blockade inhibitor or an anti-tumor monoclonal antibody). In some embodiments, detecting a detectable marker is useful for assessing the endogenous immune response prior to immunotherapy, or assessing efficacy of immunotherapy during administration, for example by having an enzyme-susceptible substrate with readout that is in the urine.

In some embodiments, a protease detected by methods and compositions described herein is associated with a pathogenic agent and is thus indicative of infection in a subject. Accordingly, in some aspects, the disclosure provide a method for identifying a pathogenic agent comprising administering to the lymph node of a subject infected or suspected of being infected with a pathogenic agent a lymph node biomarker nanoparticle, wherein the lymph node biomarker nanoparticle comprises a modular structure having a carrier domain linked to a lymph node specific enzyme susceptible detectable marker, wherein the lymph node specific enzyme susceptible detectable marker is comprised of an enzyme susceptible domain linked to a detectable marker whereby the detectable marker is capable of being released from the biomarker nanoparticle when exposed to an enzyme associated with a pathogenic agent; obtaining a urine sample from the subject for detection of the marker; and, analyzing the urine sample using a capture assay in order to detect the presence of the detectable marker, wherein the presence of the detectable marker in the urine sample is indicative of the subject being infected with the pathogenic agent.

Examples of infectious diseases that can be detected by methods and compositions of the disclosure include but are not limited to bacterial infections, viral infections, fungal infections, and parasitic infections.

Administration

Compositions described herein can be administered to any suitable subject. As used herein, a subject is a human, non-human primate, cow, horse, pig, sheep, goat, dog, cat, or rodent. In all embodiments human subjects are preferred. In aspects of the invention pertaining to cancer diagnosis in general the subject preferably is a human suspected of having cancer, or a human having been previously diagnosed as having cancer. Methods for identifying subjects suspected of having cancer may include physical examination, subject's family medical history, subject's medical history, biopsy, or a number of imaging technologies such as ultrasonography, computed tomography, magnetic resonance imaging, magnetic resonance spectroscopy, or positron emission tomography.

As used herein, a biological sample is a tissue sample. The biological sample may be examined in the body, for instance, by detecting a label at the site of the tissue, i.e. urine. Alternatively the biological sample may be collected from the subject and examined in vitro. Biological samples include but are not limited to urine, blood, saliva, or mucous secretion. In preferred embodiments the tissue sample is obtained non-invasively, such as the urine.

A "plurality" of elements, as used throughout the application refers to 2 or more of the elements.

The biomarker nanoparticles of the invention are administered to the subject in an effective amount for detecting enzyme activity. An "effective amount", for instance, is an amount necessary or sufficient to cause release of a detectable level of detectable marker in the presence of an enzyme. The effective amount of a compound of the invention described herein may vary depending upon the specific compound used, the mode of delivery of the compound, and whether it is used alone or in combination. The effective amount for any particular application can also vary depending on such factors as the disease being assessed or treated, the particular compound being administered, the size of the subject, or the severity of the disease or condition as well as the detection method. One of ordinary skill in the art can empirically determine the effective amount of a particular molecule of the invention without necessitating undue experimentation. Combined with the teachings provided herein, by choosing among the various active compounds and weighing factors such as potency, relative bioavailability, patient body weight, severity of adverse side-effects and preferred mode of administration, an effective regimen can be planned.

Pharmaceutical compositions of the present invention comprise an effective amount of one or more agents, dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences (1990), incorporated herein by reference). Except insofar as any conventional carrier is incompatible with the active ingredient, its use in the therapeutic or pharmaceutical compositions is contemplated. The agent may comprise different types of carriers depending on whether it is to be administered in solid, liquid or aerosol form, and whether it need to be sterile for such routes of administration as injection.

Aspects of the disclosure relate to the discovery that, in some embodiments, lymph node biomarker nanoparticles circulate and sense the lymph node microenvironment after systemic administration to a subject. In some embodiments, the systemic administration is injection, optionally subcutaneous injection. Preferably the material is injected into the body but could also be administered by other routes. For instance, the compounds of the present invention can be administered intravenously, intradermally, intraarterially, intralesionally, intratumorally, intracranially, intraarticularly, intraprostaticaly, intrapleurally, intratracheally, intranasally, intravitreally, intravaginally, intrarectally, topically, intratumorally, intramuscularly, intraperitoneally, subcutaneously, subconjunctival, intravesicularlly, mucosally, intrapericardially, intraumbilically, intraocularally, orally, topically, locally, inhalation (e.g., aerosol inhalation), injection, infusion, continuous infusion, localized perfusion bathing target cells directly, via a catheter, via a lavage, in creams, in lipid compositions (e.g., liposomes), or by other method or any combination of the forgoing as would be known to one of ordinary skill in the art (see, for example, Remington's Pharmaceutical Sciences (1990), incorporated herein by reference).

EXAMPLE

Lymph nodes adjacent to tumors integrate several useful diagnostic signals and may serve as the first stop for metastatic tumor cells, and thus are valuable in staging the invasiveness of a patient's cancer. Nodes also house the coordinated immune response against the tumor and, if molecularly probed, could provide a snapshot view of the current state of tumor immunity in a patient. In spite of this potentially rich source of information, the only current way to functionally probe lymph nodes is via invasive surgical removal, associated with significant morbidity to patients, and subsequent traditional histopathological analysis. Less invasive imaging modalities can help determine whether tumor cells are present in the lymph node, but they fail to provide information regarding invasiveness or immune activity. If clinicians had access to these data, they could make more informed decisions on: whether surgical lymph node excision is required, which nodes to remove, how invasive the tumor is, how well the patient may respond to immunotherapy, and whether additional interventions should be prescribed, etc.

The following Examples describe some embodiments of approaches for highly multiplexed protease-sensitive nanosensors developed to probe the multitude of signals at the lymph node. Protease cleavage of substrates is assessed via urine measurement of reporter fragments to provide a minimally invasive snapshot of the current state of the node. Peptide substrates are tethered (e.g., conjugated) to serum albumin, which serves the dual purpose of targeting the lymph node via high molecular weight-mediated uptake and excluding injected material from renal filtration prior to proteolytic activation. Only after substrates encounter their cognate proteases are they liberated from their protein carrier, enter the bloodstream and get concentrated in the urine. The development of these urinary monitoring tools for lymph node activity enables physicians to noninvasively monitor cancer progression, stage invasiveness, and understand the immune response.

Lymph Node Specific Synthetic Biomarkers

Aberrantly expressed proteases are candidate enzymes for cancer detection and analysis because they play critical roles in many cancers. Additionally, proteases are involved in many immune processes, including immune cell trafficking to and from the lymph node and target cell killing (FIG. 1). A set of protease-sensitive substrates is delivered to the lymph node using recently acquired knowledge on trafficking carriers to lymph nodes. Upon encountering their cognate proteases, the protease-sensitive substrates are cleaved and reporter fragments are excreted into urine, providing a non-invasive diagnostic readout. A subset of the delivered substrates will be responsive to proteases enriched in different stages of tumor invasiveness (e.g., metastasis), and provide the clinician with a high resolution, functionality driven snapshot of lymph node (LN) metastases. The remaining substrates are reactive against immunological proteolytic activity, providing oncologists with an understanding of the ongoing anti-tumor immune response. Together, the two substrate sets provide next-generation functional diagnostics for LN monitoring.

Figure 2A:
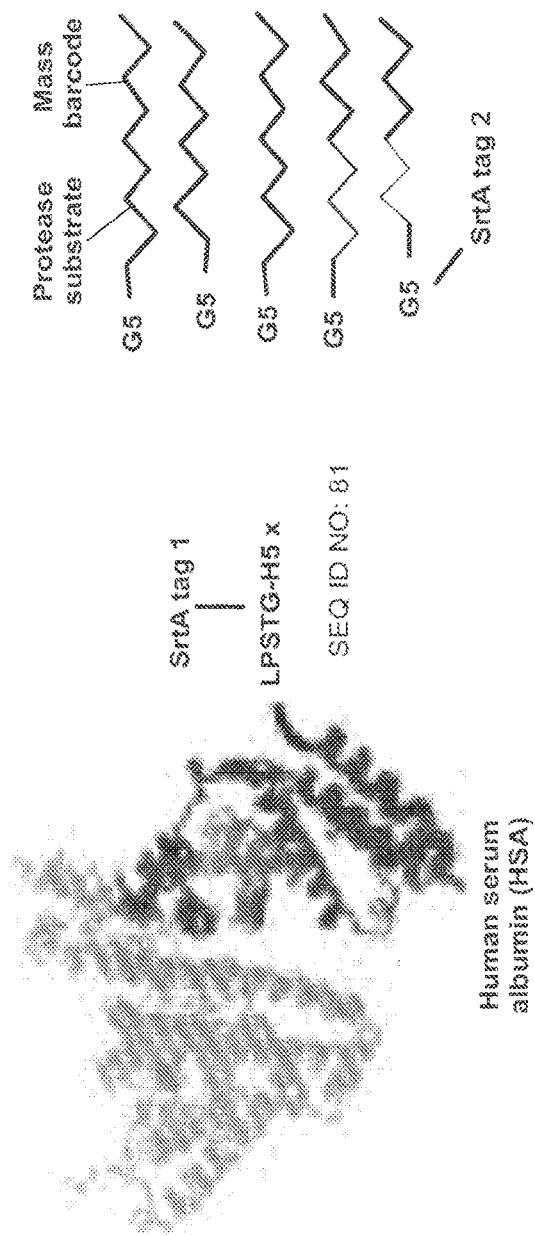
FIGS. 2A-2B describe one embodiment of an approach for lymph node monitoring.
Figure 2B:
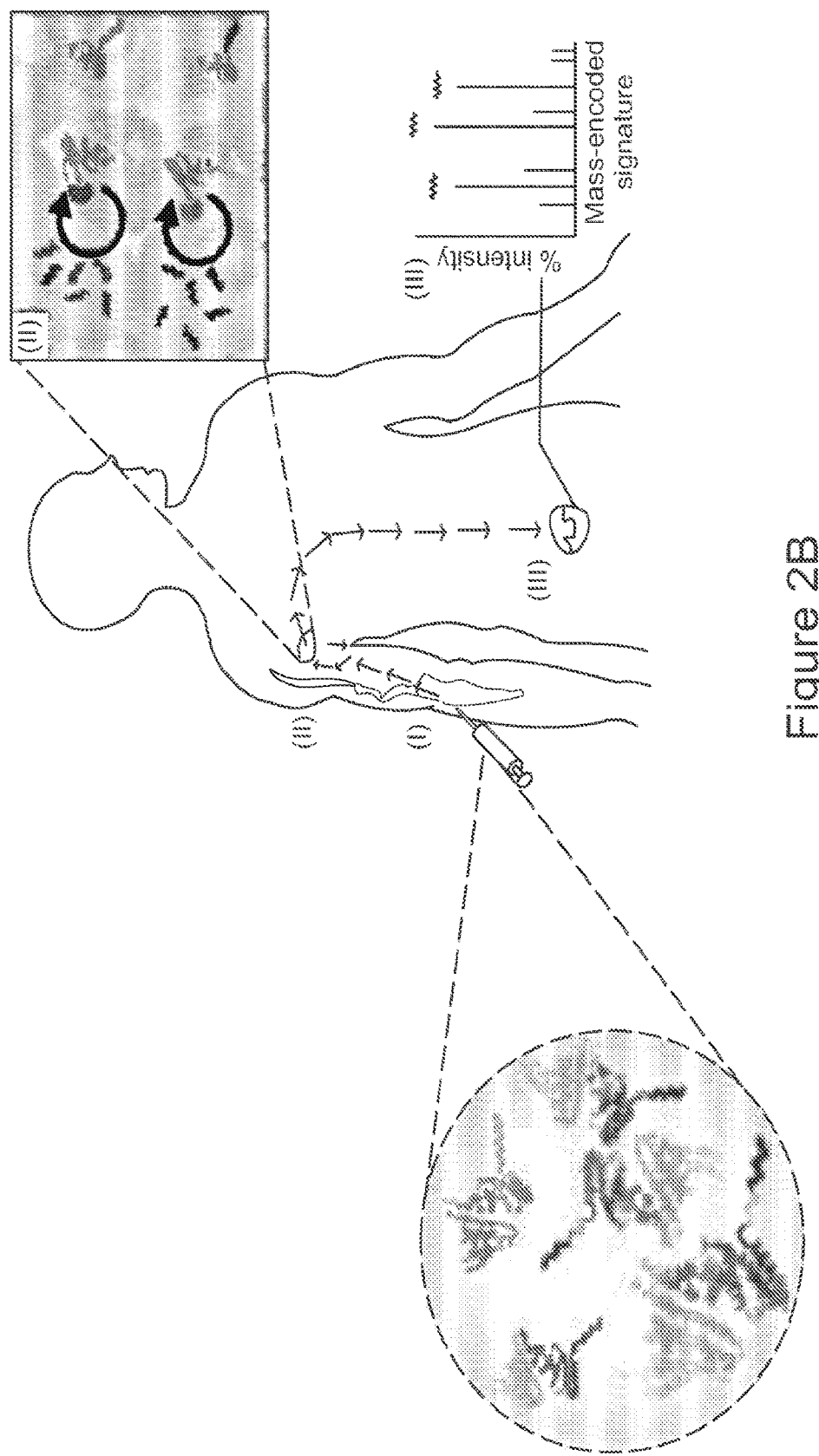

This Example describes multiplexed, protease nanosensors with urinary readouts that accumulate in primary tumors called 'synthetic biomarkers'. This example also describes protein carriers that have optimized pharmacokinetic properties such that there is minimal accumulation in the blood stream and other high background organs such as the liver, following subcutaneous injection. The protease nanosensors can be designed to be cleaved by various metastasis-associated proteases. Proteolytic cleavage liberates urinary fragments. which can be detected by mass spectrometry (FIGS. 2A-2B). In some embodiments, delivery of multiplexed, proteolytically-activated sensors described by the disclosure to tumor-draining lymph nodes is useful for diagnosis and prognosis of LN tumor metastasis, or LN immune response, by 1) detecting and characterizing LN metastases via the presence of aberrantly expressed proteases in migratory tumor cells, and 2) defining the localized response via the characterization of immune-associated proteolytic activity. Substrate libraries that profile the proteases involved in tumor metastasis in the lymph node and immune-associated proteases are also produced.

Figure 3A:
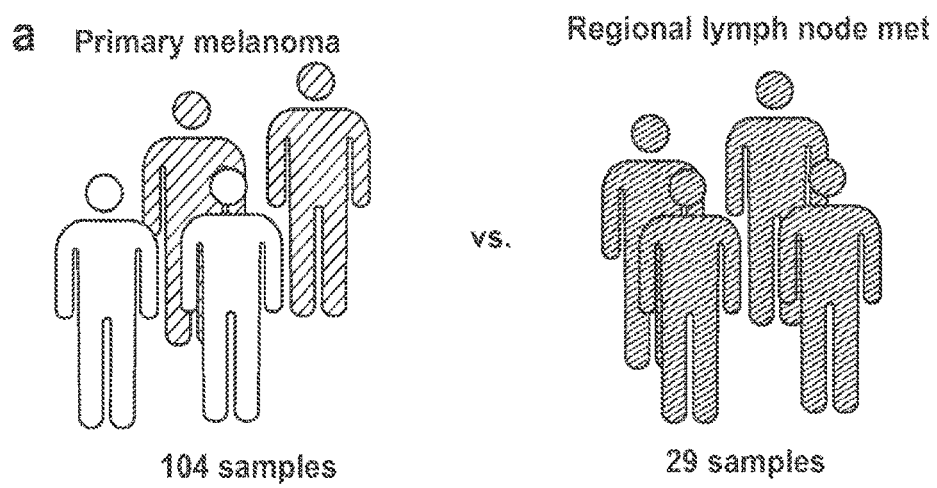
FIGS. 3A-3B show TCGA (the Cancer Genome Atlas) analysis reveals lymph node metastases specific protease profiles.
Figure 3B:
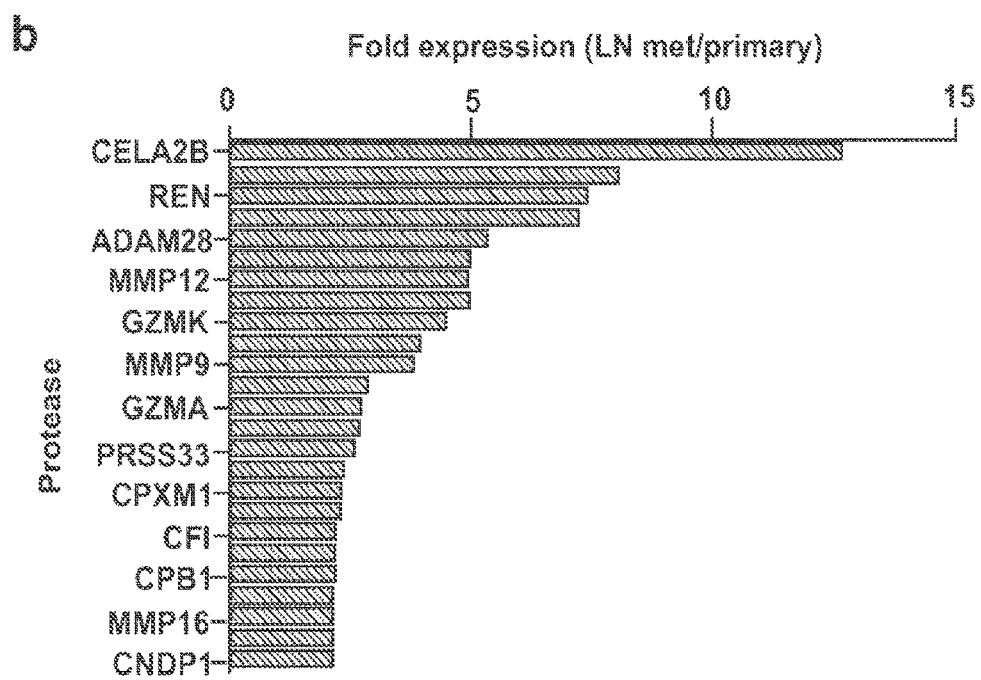

Identification of Protease Signatures for LN Metastases and Immunological Activity Candidate proteases are identified by analyzing available RNA transcript data from melanoma samples (e.g., FIG. 3A) to identify lymph node metastasis specific protease profiles. Analysis of these data sets identified candidate proteases including but not limited to ADAM28, MMP9, and MMP12 (FIG. 3B). Immune-related proteases are also identified, such as proteases involved in immune cell trafficking and target cell killing, e.g., granzymes A, B, K and Cathepsin D (FIG. 1). Additional candidate proteases upregulated in lymph nodes of melanoma samples versus primary samples are shown in Table 3.

TABLE 3

Proteases upregulated in RLN samples vs Primary samples from TCGA (the Cancer Genome Atlas) melanoma.

| Gene Name | Score(d) | Numerator(r) | Denominator(s + s0) | Fold Change | q-value(%) |
|---|---|---|---|---|---|
| ADAM28 | 5.6187932246625 | 291.571949602122 | 51.8922725830751 | 5.27392286943209 | 0 |
| MMP9 | 5.02194664053601 | 5776.7374005305 | 1150.29844281936 | 3.71777599185352 | 0 |
| ACE | 4.98939405175635 | 492.792108753316 | 98.7679272555842 | 2.04458307299482 | 0 |
| ADAMDEC1 | 4.48371075384786 | 735.351127320955 | 164.005032369647 | 4.89371810199986 | 0 |
| GZMK | 4.31642234597524 | 736.148209549072 | 170.545917554958 | 4.44288410276132 | 0 |
| MMP12 | 4.07535661102745 | 292.520225464191 | 71.7778229941068 | 4.91482479066734 | 0 |
| GZMA | 3.78388726532043 | 443.168103448276 | 117.119795695273 | 2.60786613495973 | 0 |
| ADAMTS5 | 3.37780765594101 | 188.777519893899 | 55.8875871933888 | 2.15412745100027 | 0 |
| HTRA4 | 3.20241223082401 | 36.8902519893899 | 11.5195200774941 | 2.59392862770941 | 0 |
| C2 | 2.96774560381754 | 4676.8775596817 | 1575.90244718605 | 2.05768709894241 | 0 |
| REN | 2.94443698992391 | 11.9429708222812 | 4.05611356709311 | 7.33708655876144 | 0 |
| CPA5 | 2.67466496680941 | 7.01442307692308 | 2.62254269748429 | 3.85652752760592 | 4.76798637718178 |
| CELA1 | 2.55069771166091 | 0.875 | 0.343043393970129 | 8 | 4.76798637718178 |
| MMP16 | 2.46556009729632 | 901.373342175066 | 365.585630284776 | 2.05725788449019 | 4.76798637718178 |
| CFI | 2.32517417765658 | 1254.27884615385 | 539.434360748823 | 2.12317998260705 | 4.76798637718178 |

TABLE 3-continued

Proteases upregulated in RLN samples vs Primary samples from TCGA (the Cancer Genome Atlas) melanoma.

| Gene Name | Score(d) | Numerator(r) | Denominator(s + s0) | Fold Change | q-value(%) |
|---|---|---|---|---|---|
| KLK3 | 1.90207476848199 | 51.1147214854111 | 26.8731399692583 | 25.8407992265549 | 9.34267600934268 |
| CPA1 | 1.84692635626155 | 1.40285145888594 | 0.759560040999966 | 4.94315004659832 | 10.636277302944 |
| ADAMTS6 | 1.80305667900417 | 59.3975464190981 | 32.9426950970302 | 2.10526835347758 | 10.636277302944 |
| CPXM1 | 1.57925185321327 | 1431.01956233422 | 906.13764956017 | 2.18816540778367 | 15.1761517615176 |
| PRSS33 | 1.22734278806856 | 680.528183023873 | 554.472792474549 | 2.50013631137758 | 22.2222222222222 |
| CNDP1 | 1.13296586861481 | 416.114088196286 | 367.278573629969 | 2.02808193732172 | 22.2222222222222 |
| CPB1 | 1.02787802609301 | 8.97049071618037 | 8.72719378025565 | 2.09370578485669 | 27.7676583687513 |
| KLK15 | 1.01409062889863 | 2.18866047745358 | 2.15824938628079 | 2.7375625164517 | 27.7676583687513 |
| CELA2B | 0.867216607521151 | 0.222148541114058 | 0.25616269244318 | 12.551724137931 | 33.2033788174139 |
| RELN | 0.806346488754898 | 345.229442970822 | 428.140319062963 | 2.22371718026467 | 33.2033788174139 |
| PRSS58 | 0.293044921192387 | 0.0593501326259947 | 0.20252912892843 | 7.17241379310345 | 34.1189674523008 |

Optimization and Characterization of In Vivo Pharmacokinetic Properties of Protein-Delivered Synthetic Biomarkers It has been observed that subcutaneous injection of protein carriers enables robust trafficking to the lymph nodes in the vicinity of that injection. In particular, data indicate that serum albumin is an exceptionally effective chaperone to deliver peptides to lymph nodes. Synthetic peptides conjugated to albumin are recombinantly produced by reacting serum albumin functionalized with the C-terminal Sortase A recognition motif LPSTG with (G)5-modified protease-sensitive peptide probes to albumin (FIG. 2A). Sortase A is a transpeptidase that enables robust bioconjugation between expressed proteins and synthetic peptides. Here, albumin serves a dual purpose, as it both improves LN uptake and anchors the synthetic biomarkers (e.g., urinary synthetic biomarkers) to a protein that is renally excluded (e.g., serum albumin) prior to proteolytic processing.

Figure 4A:
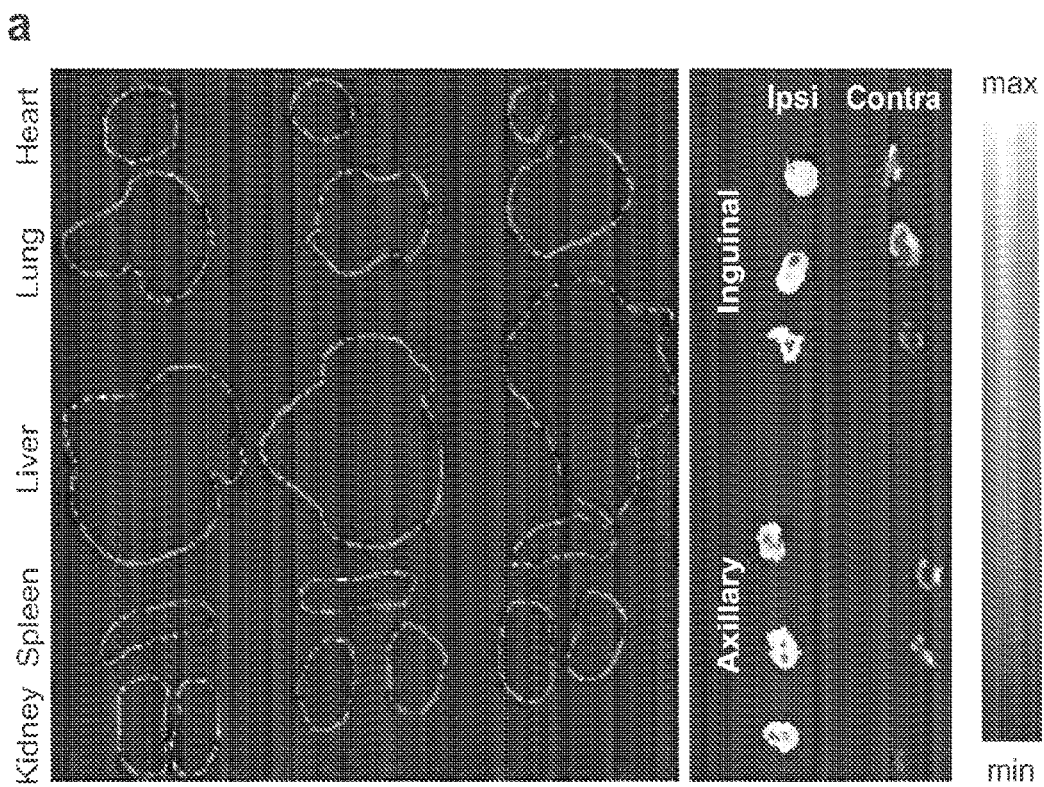
FIGS. 4A-4B show that albumin-conjugated synthetic biomarkers efficiently and selectively target lymph nodes.
Figure 4B:
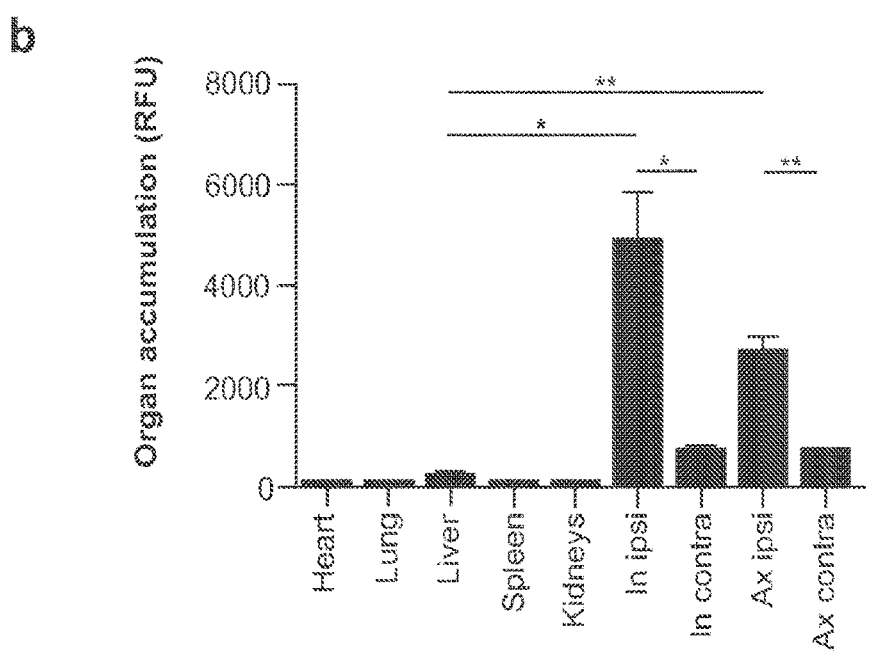

The pharmacokinetic properties of albumin-chaperoned synthetic biomarkers are tested by injecting them into a subject subcutaneously and measuring blood accumulation and end-point biodistribution. Pharmacokinetic data indicate over 30-fold higher average accumulation in inguinal lymph nodes than the liver (FIGS. 4A-4B).

Other carrier proteins can also be used, for example, antibodies that efficiently drain to the lymph node. Antibody-delivered synthetic biomarkers, in some embodiments, exhibit improved sensitivity due to targeting characteristics and may be multifunctional in their ability to both detect and deplete LN metastases.

Figure 5:
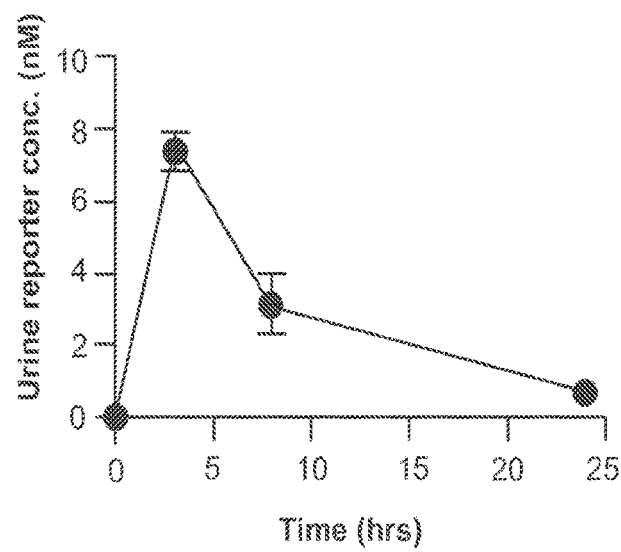
FIG. 5 shows urine concentration of reporters after subcutaneous injection of Albumin-B7 in healthy mice shows peak urine signal at 3 hours post-injection with detectable signal 24 hours post-injection.

Synthetic biomarker accumulation was also measured in the urine. Healthy mice were administered Albumin-B7 peptide (Albumin-GPLGVRGKGK(Biotin)eGvndneeGffsarK(FAM)) (SEQ ID NO: 75) where the protease cleavable substrate is PLGVRGK (SEQ ID NO: 76) and urinary reporter is ligand coded K(Biotin)eGvndneeGffsarK(FAM) (SEQ ID NO: 77) for detection with ELISA. Lowercase residues indicate $_D$-forms of each amino acid. FIG. 5 shows urine concentration of reporters after subcutaneous injection of Albumin-B7 in healthy mice shows peak urine signal at 3 hours post-injection with detectable signal 24 hours post-injection.

Urinary Monitoring of Vaccine Efficacy

Figure 6:
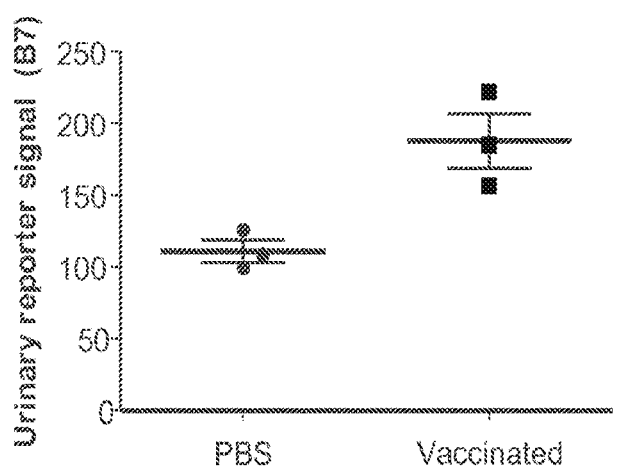
FIG. 6 shows quantification of urinary reporter signal (B7) in mice vaccinated with a cancer-specific peptide vaccine and adjuvant to stimulate immune response in the lymph nodes. Mice were injected subcutaneously and urine for analysis was collected 3 h post-administration.

Mice were subcutaneously injected with a cancer-specific peptide vaccine amph-EGP (DSPE-PEG2000-maleimide conjugated to CAVGALEGPRNQDWLGVPRQL (SEQ ID NO: 78)), or PBS, and lymph node-targeting adjuvant (lipo-CpG (DSPE conjugated to class B CpG 1826: 5'-tc-catgacgttcctgacgtt-3'; SEQ ID NO: 79)) to stimulate immune response in the lymph nodes. Mice were later boosted to engage both innate and adaptive immunity. Subsequently, mice were administered a LN-targeting pro-diagnostic reagent comprising a LN-specific enzyme susceptible domain (e.g., protease substrate). Cleavage of the pro-diagnostic reagent by metalloproteases in the LN results in production of signature molecules (ligand encoded tags) that are released into the urine of the subject (e.g., mouse). Urine was collected from the mice 3 hours after injection. Reporter signal was quantified by ELISA. Data indicate that reporter signal in vaccinated mice was significantly increased compared to PBS-injected mice, as shown in FIG. 6.

Ex Vvo Peptide Screen of LN From Vaccinated Mice and Control Mice

Figure 7:
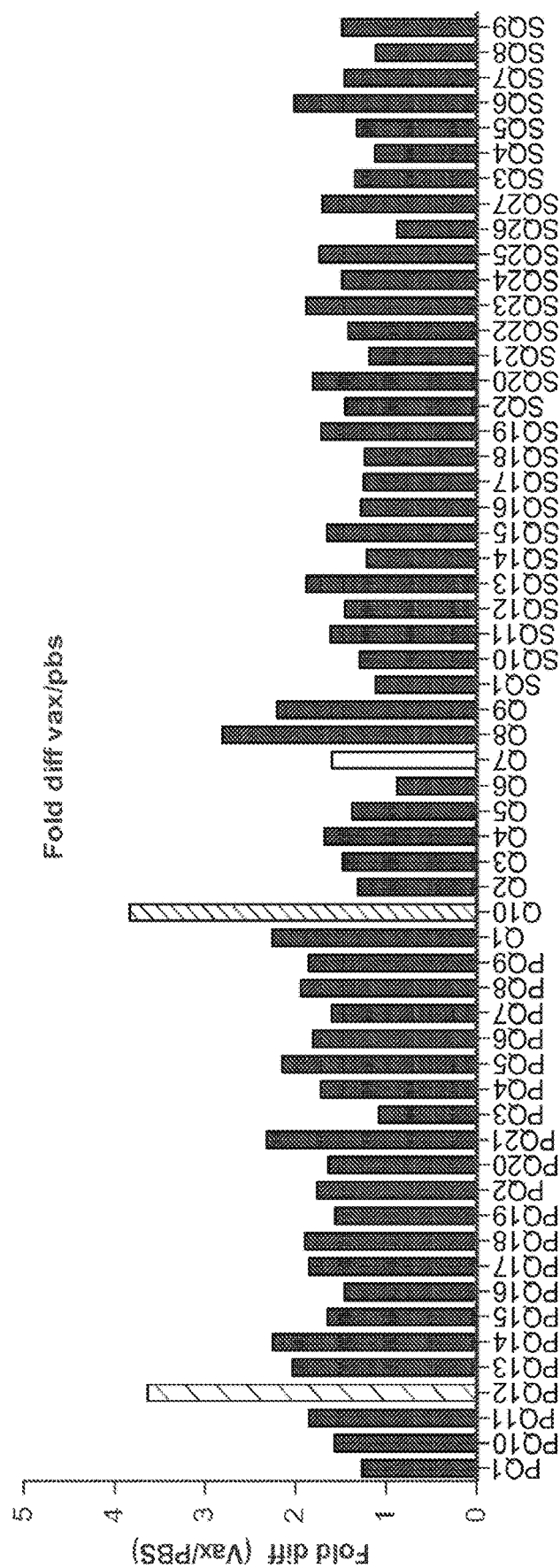
FIG. 7 shows an ex vivo peptide screen of lymph nodes from vaccinated mice versus control mice. Substrate cleavage of 58 peptides was measured. Signal reported is the fold difference in cleavage between vaccinated mice and PBS-injected mice.

Mice were vaccinated in the same manner as described above. Lymph nodes from vaccinated or non-vaccinated mice were harvested. The harvested lymph nodes were homogenized and added to the 58 fluorogenic protease substrates (SEQ ID NOs: 2-59) in 384 well plates. Fluorescent signal was monitored over the period of several hours for each substrate in the well plates. Fluorescence of reporter molecules in lymph nodes of vaccinated mice was compared to non-vaccinated mice (injected with PBS) and reported as the fold difference in cleavage of each substrate between vaccinated and control mice. Data indicate that the two highest cleaved substrates in the LN of vaccinated mice are PQ12 (GGVPRG; SEQ ID NO: 74) and Q10 (f(Pip)KSGGG, where f is a D stereoisomer of Phe and Pip is pipecolic acid; SEQ ID NO: 80) (FIG. 7). The substrate used urinary monitoring experiment described above is referred to as Q7 (PLGVRGK; SEQ ID NO: 76).

Multiplexed Synthetic Biomarker Library for Lymph Node Monitoring

One embodiment of an approach for mass-encoding protease substrate-urinary reporter tandems is described. A 10-plex albumin-chaperoned library (e.g., an albumin-chaperoned library having mass-encoded reporters) that responds to both metastasis-associated and immune-associated proteases is produced. These albumin-synthetic biomarkers are tested in murine models of melanoma. Melanoma cells are injected into the flank of mice and allowed to metastasize to the lymph node. Sensors are infused into mice and urine is collected at various timepoints. Cleavage patterns are monitored from the mass-encoded reporters using LC-MS/MS and analyzed for evolving signatures that classify lymph node metastasis.

To demonstrate classification between different indications, the immune system of non-tumor bearing mice is examined. Similarly, the proteolytic signatures identified by the platform that identify immune response are examined. In some cases, the signatures identified from metastasis are non-overlapping from the signatures identified from immune stimulation.

The specificity of lymph node sampling is tested using a mouse model of lung metastatic cancer as a negative control. There is minimal lymph node involvement in this model because the sensors should not respond to increased proteolysis occurring in the lungs.

The invention claimed is:

1. A composition for detecting the activity of a granzyme present in a lymph node, comprising:
    a lymph node biomarker nanoparticle, wherein the lymph node biomarker nanoparticle comprises a modular structure having a carrier domain comprising a lymph node trafficking carrier linked via a substrate for the granzyme to a detectable marker, wherein the lymph node trafficking carrier accumulates more of the lymph node biomarker nanoparticle in the lymph node of a subject as compared to the subject's liver, whereby when the biomarker nanoparticle is exposed to the granzyme in the lymph node in the subject, the detectable marker is released from the carrier domain, enters the subject's bloodstream, is excreted in urine from the subject, and is detectable ex vivo in the urine.

2. The composition of claim 1, wherein the lymph node trafficking carrier accumulates the lymph node biomarker nanoparticle at least 30-fold more in the lymph node of the subject as compared to the subject's liver.

3. The composition of claim 1, wherein the lymph node trafficking carrier is albumin or an albumin-binding peptide.

4. The composition of claim 1, wherein the lymph node trafficking carrier is an antibody.

5. The composition of claim 1, wherein the lymph node trafficking carrier is a protein, a polymer, or a nanoparticle carrier and wherein the protein, polymer or carrier is greater than about 40 kDa.

6. The composition of claim 1, wherein the lymph node biomarker nanoparticle further comprises a cancer substrate linked to a second detectable marker.

7. The composition of claim 1, wherein the lymph node biomarker nanoparticle further comprises a metastatic cancer substrate.

8. The composition of claim 1, wherein the detectable marker comprises two immune-associated substrates.

9. The composition of claim 6, wherein the cancer substrate is a substrate for a protease selected from ADAM28, MMP9, and MMP12.

10. The composition of claim 8, wherein at least one of the immune-associated substrates is a substrate for Cathepsin D.

11. The composition of claim 1, wherein the substrate for the granzyme comprises SEQ ID NO: 71, SEQ ID NO: 72, or SEQ ID NO: 73.

12. A composition for detecting the activity of a granzyme present in a lymph node, comprising:
    a lymph node biomarker nanoparticle comprising a lymph node trafficking carrier domain linked via a granzyme substrate to a detectable marker that, when the biomarker nanoparticle is exposed to the granzyme in the lymph node in a subject, said detectable marker is released from the carrier domain, enters the subject's reticuloendothelial system, is excreted in urine from the subject, and is detectable ex vivo in the urine and wherein the lymph node trafficking carrier domain accumulates more of the lymph node biomarker nanoparticle in the lymph node of a subject as compared to the subject's liver.

13. The composition of claim 12, wherein the lymph node trafficking carrier domain comprises albumin or an albumin-binding peptide.

14. The composition of claim 12, wherein the lymph node trafficking carrier accumulates the lymph node biomarker nanoparticle at least 30-fold more in the lymph node of the subject as compared to the subject's liver.

15. A composition comprising:
a lymph node biomarker nanoparticle, wherein the lymph node biomarker nanoparticle comprises a modular structure having a carrier domain comprising a lymph node trafficking carrier linked to an enzyme susceptible detectable marker, wherein the lymph node trafficking carrier accumulates more of the lymph node biomarker nanoparticle in a lymph node of a subject as compared to the subject's liver, wherein the enzyme susceptible detectable marker is comprised of a substrate for a granzyme linked to a detectable marker whereby when the biomarker nanoparticle is exposed to the granzyme at the lymph node in the subject, the detectable marker is released from the biomarker nanoparticle, enters the subject's bloodstream, is excreted in urine from the subject, and is detectable ex vivo in the urine, wherein substrate for the granzyme comprises SEQ ID NO: 71, SEQ ID NO: 72, or SEQ ID NO: 73.

16. A composition comprising:
a lymph node biomarker nanoparticle comprising a lymph node trafficking carrier domain linked via a granzyme substrate to a detectable marker that, when the biomarker nanoparticle is exposed to the granzyme at a lymph node in a subject, is released from the carrier domain, enters the subject's reticuloendothelial system, is excreted in urine from the subject, and is detectable ex vivo in the urine and wherein the lymph node trafficking carrier domain accumulates more of the lymph node biomarker nanoparticle in the lymph node of the subject as compared to the subject's liver, wherein granzyme substrate comprises SEQ ID NO: 71, SEQ ID NO: 72, or SEQ ID NO: 73.

* * * * *